(12) United States Patent
Nakashima et al.

(10) Patent No.: US 10,196,500 B2
(45) Date of Patent: Feb. 5, 2019

(54) PARTICULATE WATER ABSORBING AGENT AND PROCESS FOR PRODUCING SAME

(71) Applicant: NIPPON SHOKUBAI CO., LTD., Osaka (JP)

(72) Inventors: Yasuhisa Nakashima, Himeji (JP); Katsuyuki Wada, Himeji (JP); Hiroyuki Ikeuchi, Himeji (JP); Manabu Ueda, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 359 days.

(21) Appl. No.: 14/423,588

(22) PCT Filed: Aug. 27, 2013

(86) PCT No.: PCT/JP2013/072880
§ 371 (c)(1),
(2) Date: Feb. 24, 2015

(87) PCT Pub. No.: WO2014/034667
PCT Pub. Date: Mar. 6, 2014

(65) Prior Publication Data
US 2015/0218341 A1 Aug. 6, 2015

(30) Foreign Application Priority Data
Aug. 27, 2012 (JP) ................. 2012-186007

(51) Int. Cl.
| C08L 33/02 | (2006.01) |
| C08K 5/13 | (2006.01) |
| G01N 15/06 | (2006.01) |
| C02F 1/28 | (2006.01) |
| B01J 20/22 | (2006.01) |
| B01J 20/26 | (2006.01) |
| C08J 3/24 | (2006.01) |
| A61L 26/00 | (2006.01) |
| A61L 15/22 | (2006.01) |
| A61L 15/42 | (2006.01) |
| A61L 15/48 | (2006.01) |
| A61L 15/60 | (2006.01) |
| C08K 5/00 | (2006.01) |
| C08K 3/011 | (2018.01) |

(52) U.S. Cl.
CPC .............. *C08K 5/13* (2013.01); *A61L 15/225* (2013.01); *A61L 15/42* (2013.01); *A61L 15/48* (2013.01); *A61L 15/60* (2013.01); *A61L 26/008* (2013.01); *A61L 26/0014* (2013.01); *A61L 26/0061* (2013.01); *B01J 20/223* (2013.01); *B01J 20/267* (2013.01); *C02F 1/285* (2013.01); *C08J 3/245* (2013.01); *C08L 33/02* (2013.01); *G01N 15/06* (2013.01); *B01J 2220/445* (2013.01); *C08J 2333/02* (2013.01); *C08K 3/011* (2018.01); *C08K 5/005* (2013.01); *Y02W 10/37* (2015.05)

(58) Field of Classification Search
None
See application file for complete search history.

(56) References Cited

U.S. PATENT DOCUMENTS

| 4,734,478 A | 3/1988 | Tsubakimoto et al. | |
| 5,244,735 A | 9/1993 | Kimura et al. | |
| 5,668,078 A | 9/1997 | Sumiya et al. | |
| 5,681,878 A | 10/1997 | Klotzsche et al. | |
| 6,605,673 B1 | 8/2003 | Mertens et al. | |
| 2001/0007898 A1* | 7/2001 | Inagakai | C08F 8/44 |
| | | | 528/154 |
| 2005/0288182 A1 | 12/2005 | Torii et al. | |
| 2006/0073969 A1 | 4/2006 | Torii et al. | |
| 2006/0204755 A1 | 9/2006 | Torii et al. | |
| 2006/0247351 A1* | 11/2006 | Torii | C08J 3/245 |
| | | | 524/406 |
| 2007/0066754 A1 | 3/2007 | Loeker et al. | |
| 2007/0106239 A1 | 5/2007 | Riegel et al. | |

(Continued)

FOREIGN PATENT DOCUMENTS

| CN | 85105605 A | 4/1986 |
| CN | 101155870 A | 4/2008 |

(Continued)

OTHER PUBLICATIONS

Chinese Office Acton dated Dec. 11, 2015 that issued in the counterpart Patent Application No. 201380044697.6, including English translation.
Buchholz, F. et al., Modern Superabsorbent Polymer Technology, Wiley-VCR, 1998, pp. 39-44.
International Preliminary Report on Patentability for PCT/JP2013/072880, dated Mar. 12, 2015.
International Search Report for PCT/JP2013/072880, dated Dec. 3, 2013, and English translation thereof.

(Continued)

Primary Examiner — Joseph D Anthony
(74) Attorney, Agent, or Firm — Dickinson Wright PLLC

(57) ABSTRACT

The present invention (a) provides, at low cost, a water absorbing agent (i) that has a suppressed amount of generated dust and a suppressed amount of dust that increases over time and (ii) that also has a high absorption capacity without load, a high absorption capacity under load, a high vertical diffusion absorbency under load, and a high absorbency in a short period of time, and (b) also provides a method for evaluating, in a short period of time, an amount of dust that increases over time. A particulate water absorbing agent of the present invention includes: a surface cross-linked polyacrylic acid (salt)-based water absorbent resin as a main component; a hydrophilic polymer compound; and a stabilizing agent.

8 Claims, No Drawings

(56) References Cited

U.S. PATENT DOCUMENTS

| | | | |
|---|---|---|---|
| 2007/0123658 A1* | 5/2007 | Torii | A61L 15/60 525/329.7 |
| 2007/0141338 A1* | 6/2007 | Ishizaki | C08J 3/12 428/402 |
| 2008/0221277 A1 | 9/2008 | Walden et al. | |
| 2008/0280128 A1 | 11/2008 | Furno et al. | |
| 2009/0008604 A1 | 1/2009 | Nakashima et al. | |
| 2009/0023848 A1* | 1/2009 | Ahmed | A61L 15/56 524/422 |
| 2009/0105389 A1 | 4/2009 | Walden et al. | |
| 2009/0157027 A1* | 6/2009 | Kamphus | A61L 15/26 604/365 |
| 2009/0202805 A1 | 8/2009 | Furno et al. | |
| 2009/0208748 A1 | 8/2009 | Torii et al. | |
| 2009/0227741 A1 | 9/2009 | Walden et al. | |
| 2009/0275470 A1* | 11/2009 | Nagasawa | A61F 13/53 502/402 |
| 2009/0298685 A1* | 12/2009 | Torii | A61L 15/18 502/402 |
| 2010/0072421 A1* | 3/2010 | Kitano | A61L 15/24 252/194 |
| 2010/0120940 A1* | 5/2010 | Adachi | A61F 13/15 523/111 |
| 2010/0209379 A1 | 8/2010 | Furno et al. | |
| 2010/0270501 A1 | 10/2010 | Torii et al. | |
| 2010/0308263 A1 | 12/2010 | Torii et al. | |
| 2011/0009841 A1 | 1/2011 | Ahmed et al. | |
| 2011/0015601 A1 | 1/2011 | Loeker et al. | |
| 2011/0034603 A1* | 2/2011 | Fujino | A61L 15/22 524/320 |
| 2012/0083411 A1 | 4/2012 | Ahmed et al. | |
| 2012/0184670 A1* | 7/2012 | Kobayashi | C08K 5/098 524/556 |
| 2012/0289671 A1* | 11/2012 | Takaai | A61L 15/60 526/240 |
| 2013/0001468 A1 | 1/2013 | Loeker et al. | |
| 2013/0175473 A1 | 7/2013 | Wada et al. | |
| 2014/0350191 A1 | 11/2014 | Walden et al. | |
| 2015/0129799 A1 | 5/2015 | Kobayashi et al. | |

FOREIGN PATENT DOCUMENTS

| | | |
|---|---|---|
| CN | 101939383 A | 1/2011 |
| CN | 102548654 A | 7/2012 |
| EP | 0679678 | 11/1995 |
| EP | 2623198 A1 | 8/2013 |
| JP | 63-127754 A | 5/1988 |
| JP | 5-507511 | 10/1993 |
| JP | 8-10616 | 1/1996 |
| JP | 9-124879 | 5/1997 |
| JP | 10-249195 | 9/1998 |
| JP | 2005-95759 | 4/2005 |
| JP | 2005-105254 | 4/2005 |
| JP | 2005-111474 A | 4/2005 |
| JP | 2006-28481 | 2/2006 |
| JP | 2006-45498 | 2/2006 |
| JP | 2006-528544 | 12/2006 |
| JP | 2007-534785 | 11/2007 |
| JP | 2008-125716 | 6/2008 |
| JP | 2009-142728 | 7/2009 |
| JP | 2009-531158 | 9/2009 |
| JP | 2010-533766 | 10/2010 |
| JP | 2010-540685 | 12/2010 |
| WO | 91/18042 | 11/1991 |
| WO | 94/22940 | 10/1994 |
| WO | 95/027739 | 10/1995 |
| WO | 95/33558 | 12/1995 |
| WO | 97/030109 | 8/1997 |
| WO | 97/037695 | 10/1997 |
| WO | 98/048857 | 11/1998 |
| WO | 2004/096304 | 11/2004 |
| WO | WO 2005/027986 A1 | 3/2005 |
| WO | 2006/098271 | 9/2006 |
| WO | 2007/121941 | 11/2007 |
| WO | 2011/040472 | 4/2011 |
| WO | WO 2012/043821 A1 | 4/2012 |

OTHER PUBLICATIONS

Japanese Office Action dated Sep. 13, 2016, issued in counterpart Patent Application No. 2014-533019.
Chinese Office Action dated Jun. 20, 20167 in a counterpart Patent Application No. 201380044697.6, including English translation.
Supplementary Partial European Search Report dated Apr. 1, 2016 that issued in a counterpart Patent Application No. 13832733.3.

* cited by examiner

PARTICULATE WATER ABSORBING AGENT AND PROCESS FOR PRODUCING SAME

TECHNICAL FIELD

The present invention relates to a particulate water absorbing agent and a method for producing the particulate water absorbing agent. More specifically, the present invention relates to a particulate water absorbing agent containing a polyacrylic acid (salt)-based water absorbent resin as a main component, the particulate water absorbing agent having specific water absorption performances, and a method for producing the particulate water absorbing agent.

BACKGROUND ART

Presently, a water absorbing agent containing, as a main component, a water absorbent resin in addition to hydrophilic fibers such as pulp fibers is widely used as a constituent material of an absorbent article such as a disposable diaper, a sanitary napkin, and an incontinence pad.

As known absorption performances that the water absorbent resin is desired to have, there are a water absorption capacity without load, a water absorption capacity under load, a liquid permeability, a water absorbing speed, a water soluble component, a gel strength, etc. Further, many proposals have conventionally been made as to methods for measuring these physical properties and methods for improving the physical properties (methods for producing a water absorbent resin), and in addition, parameter patents (relevant to a water absorbent resin or a water absorbing agent) specifying the above physical properties.

As additional performances that are recently attracting attention other than the above physical properties, there are a gel stability (urine resistance), a powder fluidity in a moist state, a coloration resistance, a resistance to coloration over time, break resistance, a dust suppression property, etc. Many proposals have been made as to a method of maintaining essential absorption performances that a water absorbent resin is desired to have as well as having the above additional performances.

For example, Patent Literature 1 proposes an absorbent resin particle containing a urethane resin having an anion functional group, as an absorbent resin particle having a break resistance and a dust suppression property, and discloses an absorbent resin particle (i) that has a higher break resistance as compared to a conventional absorbent resin particle, (ii) that does not easily generate dust due to a fracture or a breakage, and (iii) that exhibits excellent absorption performances.

Patent Literature 2 discloses a powder absorbent polymer obtained by bonding a water-absorbing polymer particle and a fine particle having a specific particle diameter with use of a thermoplastic adhesive, as a method of providing the water-absorbing polymer particle that has excellent absorption performances and that generates less dust.

Patent Literature 3 discloses a modified water absorbent resin particle for hygiene products which water absorbent resin particle is obtained by subjecting particles made of water absorbent resin to treatment at a normal temperature with liquid organic polysiloxane. Patent Literature 3 discloses such a water absorbent resin particle, as a water absorbent resin particle that has (i) a high absorbing speed as a result of water absorbent resin particle modification that promotes uniform permeation of water, urine, menstrual blood, etc. into the water absorbent resin particle, (ii) a low moisture absorption blocking rate, (iii) a low dust generation level, and (iv) an excellent initial absorption amount under load and an excellent absorption capacity under load.

Patent Literature 4 discloses a water absorbent resin composition containing a water absorbent resin particle, a nitrogen-containing ketone compound (note that this ketone compound does not have a carboxyl group), and a quadrivalent water-soluble multivalent metal salt. Patent Literature 4 discloses such a water absorbent resin composition, as a water absorbent resin composition (i) that is excellent in absorption capacity, liquid permeability/diffusion property, and fluidity in a moist state, (ii) that has a high damage resistance, (iii) that has an excellent dust suppressing effect, and (iv) that does not easily cause segregation of an added metal compound and/or permeation of the added metal compound into the water absorbent resin particle.

Patent Literature 5 discloses a water absorbent resin composition containing a bivalent or trivalent water-soluble multivalent metal salt in place of the quadrivalent water-soluble multivalent metal salt in Patent Literature 4.

Patent Literature 6 proposes a water absorbent resin having a surface fused with a metal compound. Meanwhile, Patent Literature 7 discloses dentrimer as a dust suppressing agent.

Patent Literatures 8 through 11 disclose various dust suppressing agents for water absorbent resins. In particular, Patent Literature 8 discloses, as a dust suppressing agent, a lower aliphatic polyol whose average molecular weight is over approximately 200, a lower polyalkylene glycol (polyethylene glycol) whose average molecular weight is in a range of approximately 400 to approximately 6000, or a propylene oxide adduct (VORANOL (registered trademark, manufactured by Dow Chemical Company)) of glycerol or polyethylene glycol whose average molecular weight is in a range of approximately 400 to approximately 6000.

Patent Literatures 12 and 13 each disclose a water absorbent resin obtained by immobilizing multivalent metal salt powder with a binder.

Patent Literature 14 discloses a water-absorbing polymer having a high liquid permeability (GBP), which water-absorbing polymer is obtained by using 0.01 wt % to 5 wt % of insoluble inorganic powder and a water penetration modifier such as polyethylene glycol for surface crosslinking.

Patent Literature 15 discloses a method of reducing a dust content of a superabsorbent polymer particle composition, according to which method a contact is made with an aqueous solution of C3-C6 diol and a crosslinking compound.

Non-Patent Literature 1 discloses preparation of a water absorbent resin with use of an acrylic acid containing a predetermined amount of p-methoxyphenol (MEHQ) that is a polymerization inhibitor, and also discloses that an amount of residual MEHQ is 16 ppm to 151 ppm in a commercial water absorbent resin.

As described above, the conventional techniques have disclosed a method of reducing dusts of a water absorbent resin and a method of immobilizing fine particles, for example, a method of immobilizing a metal salt to a water absorbent resin by addition of polyethylene glycol, methoxypolyethylene glycol, polyol polyether, or the like to a surface of the water absorbent resin. However, keeping an effect of such a method for a long term has not been known as a problem.

Further, an effect, etc. caused by localization of the polymerization inhibitor on a surface of a particulate water absorbing agent has not been known. This is because the polymerization inhibitor is contained in a monomer and therefore, evenly present inside the water absorbent resin after polymerization.

CITATION LIST

Patent Literatures

Patent Literature 1
Japanese Patent Application Publication, Tokukai, No. 2008-125716 (Publication Date: Jun. 5, 2008)
Patent Literature 2
Japanese Translation of PCT International Application, Tokuhyou, No. 2006-528544 (Publication Date: Dec. 21, 2006)
Patent Literature 3
Pamphlet of PCT International Publication No. WO95/33558 (Publication Date: Dec. 14, 1995)
Patent Literature 4
Japanese Patent Application Publication, Tokukai, No. 2006-45498 (Publication Date: Feb. 16, 2006)
Patent Literature 5
Japanese Patent Application Publication, Tokukai, No. 2006-28481 (Publication Date: Feb. 2, 2006)
Patent Literature 6
Japanese Patent Application Publication, Tokukai, No. 2005-105254 (Publication Date: Apr. 21, 2005)
Patent Literature 7
Japanese Translation of PCT International Application, Tokuhyou, No. 2007-534785 (Publication Date: Nov. 29, 2007)
Patent Literature 8
European Patent Application Publication No. 0679678 (Publication Date: Nov. 2, 1995)
Patent Literature 9
Pamphlet of PCT International Publication No. WO94/22940 (Publication Date: Oct. 13, 1994)
Patent Literature 10
Pamphlet of PCT International Publication No. WO97/030109 (Publication Date: Aug. 21, 1997)
Patent Literature 11
Pamphlet of PCT International Publication No. WO97/037695 (Publication Date: Oct. 16, 1997)
Patent Literature 12
Pamphlet of PCT International Publication No. WO98/048857 (Publication Date: Nov. 5, 1998)
Patent Literature 13
Pamphlet of PCT International Publication No. WO2007/121941 (Publication Date: Nov. 1, 2007)
Patent Literature 14
Pamphlet of PCT International Publication No. WO2004/096304 (Publication Date: Nov. 11, 2004)
Patent Literature 15
Pamphlet of PCT International Publication No. WO95/027739 (Publication Date: Oct. 19, 1995)

Non-Patent Literature

Non-Patent Literature 1
Modern Superabsorbent Polymer Technology (1998), p 39-44, p 72-77

SUMMARY OF INVENTION

Technical Problem

However, there is a demand for a water absorbing agent that has a better absorption performance than a water absorbing agent obtained by the above conventional techniques and that suppresses an amount of dust generated from the water absorbing agent in a production process of an absorbent body such as a disposable diaper with use of the water absorbing agent, as compared to the water absorbing agent obtained by the above conventional techniques.

More specifically, the water absorbing agent is required to have good values of physical properties such as a centrifuge retention capacity, an absorption ability under load, a vertical diffusion absorbency under load, an absorbency in a short period of time, etc. in use of the water absorbing agent. However, such physical properties have not been reached to satisfactory levels by use of the conventional techniques. One factor that makes such physical properties unsatisfactory is that: it is difficult to simultaneously improve the centrifuge retention capacity and the absorption ability under load or the vertical diffusion absorbency under load that are important physical properties of the water absorbing agent, because one of these physical properties improves and then the other deteriorates.

Further, in the conventional techniques, in a case where fine particles such as inorganic particles are added to the water absorbent resin, there has occurred a problem that dust is generated from the fine particles. This generation of dust becomes a cause of deterioration in production efficiency in a production process of the water absorbing agent, and a cause of deterioration in physical properties of the water absorbing agent obtained as a result, and further, a cause of a problem concerning safety and health, etc.

In a case where a binder, an adhesive, or the like is used in order to suppress the above generation of dust, an absorption performance of the water absorbing agent is impaired. This consequently causes a problem that the performance of the water absorbing agent such as a disposable diaper cannot be sufficiently utilized.

For example, in Patent Literatures 1 to 3, and 7, suppression of dust that is present from the very start and/or generated due to breakage of particles is attempted by modification of the water absorbing agent with use of an additive, or the like. However, a level of dust reduction by such modification or the like is not satisfactory. Further, disadvantageously, the nature of the additive impairs the absorption performance of the water absorbing agent, and in particular, impairs a short-time absorption performance.

Further, Patent Literatures 4 to 6 have proposed a technique that achieves both a good absorption capacity without load and a good absorption performance and/or a good performance of liquid permeability under load, which absorption capacity and performance(s) have been incompatible with each other and that also achieves a smaller amount of dust. However, a level of reduction of the dust is still not sufficient.

In addition, Patent Literature 8 to 13, and 15 have proposed various additives each for providing a water absorbing agent whose dust amount is small. However, the resultant water absorbing agent could not be satisfying in terms of a requirement of simultaneously achieving a good level of reduction of the dust amount and a good absorption performance.

In other words, in the conventional techniques, it has not been possible to obtain a water absorbing agent that simultaneously achieves a good absorption performance (absorption capacity without load, absorption performance under load, vertical diffusion property under load, liquid permeability, absorbency in a short period of time, etc.) and reduction in dust amount. Therefore, conventionally, it has not been possible to solve, in particular, a problem that the dust amount increases due to addition of an additive in a case where the additive is added for the purpose of improving a liquid permeability.

Furthermore, the inventors of the present invention has found a novel problem that: even when the dust amount is reduced in production of the water absorbing agent, a dust amount generated in a production process of an absorbent body such as a diaper with use of the water absorbing agent cannot be suppressed.

Such a novel problem has been found as a result of studies on an amount of dust generated from the water absorbing agent in a production process of an absorbent body. In other words, the inventors of the present invention have accomplished the present invention as a result of finding out a demand for a water absorbing agent that has a suppressed amount of generated dust not only at the time when the water absorbing agent is produced but also at the time when an absorbent body is produced with use of the water absorbing agent.

In addition, the inventors of the present invention has accomplished the present invention by finding out that at the same time as the above demand, there has been a demand for a method for quickly evaluating an increase over time in generated dust amount of a water absorbing agent that have been produced.

In other words, an object of the present invention is (a) to provide, at low cost, a water absorbing agent (i) that has a suppressed amount of generated dust and a suppressed amount of dust that increases over time and (ii) that also has a high absorption performance (absorption capacity without load, absorption performance under load, vertical diffusion absorbency under load, absorbency in a short period of time, etc.), and also (b) to provide a method for evaluating, in a short period of time, a dust amount that increases over time.

Solution to Problem

A particulate water absorbing agent according to the present invention includes: a polyacrylic acid (salt)-based water absorbent resin as a main component; a hydrophilic polymer compound; and a stabilizing agent, the polyacrylic acid (salt)-based water absorbent resin being surface-crosslinked.

A method for producing a particulate water absorbing agent according to the present invention including a polyacrylic acid (salt)-based water absorbent resin as a main component, the method including a polymerization step of a water-soluble unsaturated monomer containing an acrylic acid (salt) as a main component, a drying step and a surface crosslinking step, the method further includes the steps of: (a) adding a hydrophilic polymer compound; and (b) adding a stabilizing agent, the steps (a) and (b) being carried out after the surface crosslinking step.

The second invention of the present application is a method for evaluating an amount of dust that increases over time. This evaluation method carries out evaluation by use of a dust amount of a particulate water absorbing agent that has been subjected to heat treatment in which the particulate water absorbing agent is stored at 60° C. for 3 weeks in a sealed container. In other words, the evaluation method of the present invention for evaluating an increase over time in dust amount of a particulate water absorbing agent, the method includes the steps of: subjecting the particulate water absorbing agent to heat treatment in which the particulate water absorbing agent is stored at 60° C. for 3 weeks in a sealed container; and evaluating an increase over time in dust amount of the particulate water absorbing agent by measuring a dust amount after the heat treatment.

Though this evaluation method does not make it possible to predict an influence caused by an unexpected accident such as a fall from a high place, a thump, or a compression, this evaluation method makes it possible to predict an outcome in consideration of factors such as normal storage and a change in temperature during transportation.

Advantageous Effects of Invention

The particulate water absorbing agent of the present invention and a production method thereof make it possible not only to suppress an amount of dust generated in a production process of the particulate water absorbing agent but also an amount of dust generated in a production process of an absorbent body such as a disposable diaper with use of the particulate water absorbing agent. Further, the particulate water absorbing agent and the production method allows obtaining an absorbent body excellent in absorption performance because it becomes possible to obtain a particulate water absorbing agent having excellent absorption characteristics.

DESCRIPTION OF EMBODIMENTS

The following description will discuss details of a particulate water absorbing agent according to the present invention and a method for producing the particulate water absorbing agent. Note, however, that the scope of the present invention is not limited to the following descriptions, and the present invention may be appropriately modified and worked in a manner other than examples described below, to the extent of being not contrary to the purpose of the present invention. Specifically, the present invention is not limited to the embodiments below, but can be variously altered by a skilled person in the art within the scope of the claims. An embodiment derived from a proper combination of technical means disclosed in respective different embodiments is also encompassed in the technical scope of the present invention. Moreover, all Non-Patent Literatures and Patent Literatures described in this specification are incorporated herein by reference.

[1] Term Definitions (1-1) "Water Absorbing Agent"

The term "water absorbing agent" in the present invention indicates an aqueous-liquid-absorbing gelatinizer (another name: fixation agent) whose main component is a water absorbent resin. In particular, a particulate aqueous-liquid-absorbing gelatinizer is referred to as "particulate water absorbing agent". Note that the term "particulate" indicates a property of having a particle form, and "particle" indicates a solid or liquid particulate small object that has a measurable size (see GLOSSARY OF TECHNICAL TERMS IN JAPANESE INDUSTRIAL STANDARDS (Kogyo Yogo Daijiten), 4th edition, page 2002).

The "aqueous liquid" is not limited to water, and can be urine, blood, sweat, feces, waste liquid, moisture, vapor, ice, a mixture of water and an organic solvent and/or an inorganic solvent, rain-water, ground water, or the like. The aqueous liquid is not limited to a particular one, as long as water is contained. The aqueous liquid can be preferably urine, menstrual blood, sweat, or other body fluid.

The "main component" indicates a component whose content is the highest in the water absorbing agent. In the particulate water absorbing agent according to the present invention, a lower limit of a content of the polyacrylic acid (salt)-based water absorbent resin (which is the main component) is preferably 70 mass % or higher, more preferably 80 mass % or higher, and particularly preferably 90 mass % or higher. Moreover, an upper limit is 100 mass %, preferably 99 mass % or lower, and more preferably 98 mass % or lower.

(1-2) "Water Absorbent Resin"

The "water absorbent resin" of the present invention indicates a water-swelling and water-insoluble polymer gelatinizer. Note that "water-swelling" indicates that CRC (water absorption capacity without load) defined in ERT441.2-02 is 5 [g/g] or higher, and "water-insoluble" indicates that Ext (water soluble component) defined in ERT470.2-02 is 0 mass % to 50 mass %.

The water absorbent resin can be designed as appropriate in accordance with its purpose of use, and is not limited to a particular one. The water absorbent resin is preferably a hydrophilic crosslinked polymer which has been obtained by crosslinking and polymerizing unsaturated monomers each of which has a carboxyl group. Moreover, the water absorbent resin is not limited to a form in which the water absorbent resin is wholly (i.e., 100 mass %) a polymer, and can be a water absorbent resin composition that contains an additive and the like within a range in which the above described performance is maintained.

The water absorbent resin is not limited to a particular form, but may have a sheet form, a fiber form, a powder form, a film form, and a gel form, or the like form. Regardless of whether or not being surface crosslinked, water absorbent resins in such forms are collectively referred to as "water absorbent resin". Note that, according to the present invention, in order to distinguish between water absorbent resins before and after surface crosslinking, a water absorbent resin before surface crosslinking is referred to as "water absorbent resin particle" and a water absorbent resin after surface crosslinking is referred to as "water absorbent resin powder".

(1-3) "Polyacrylic Acid (Salt)-Based Water Absorbent Resin"

The "polyacrylic acid (salt)-based water absorbent resin" of the present invention indicates a crosslinked polymer that arbitrarily contains a graft component and also contains, as a main component, acrylic acid and/or salt thereof (hereinafter, referred to as "acrylic acid (salt)") as a repeating unit. Specifically, "polyacrylic acid (salt)-based water absorbent resin" indicates a polymer that contains preferably 30 mol % to 100 mol % of acrylic acid (salt) as a monomer other than a crosslinking agent.

(1-4) "EDANA" and "ERT"

"EDANA" is an abbreviation for "European Disposables and Nonwovens Associations", and "ERT" is an abbreviation for "EDANA Recommended Test Methods" which is a European standard (which is substantially an international standard) method for measuring water absorbent resin. In the present invention, measurement is carried out according to the ERT original copy (revised in 2002/publicly known document), unless otherwise noted.

(a) "CRC" (ERT441.2-02) "CRC" is an abbreviation for Centrifuge Retention Capacity, and means water absorption capacity (hereinafter, also referred to as "water absorption capacity", and being synonymous with "absorbency") without load of the water absorbent resin. Specifically, "CRC" is water absorption capacity (unit; [g/g]) measured when 0.200 g of a water absorbent resin in a nonwoven fabric bag (i) has been soaked (freely swollen) in a large excess of a 0.9 mass % sodium chloride aqueous solution for 30 minutes and (ii) then is drained by a centrifugal separator.

(b) "FSC" (ERT442.2-02)

"FSC" is an abbreviation for Free Swell Capacity, and means water absorption capacity without load after hanging of the water absorbent resin. Specifically, "FSC" is water absorption capacity (unit; [g/g]) measured when 0.200 g of a water absorbent resin in a nonwoven fabric bag (i) has been soaked (freely swollen) in a large excess of a 0.9 mass % sodium chloride aqueous solution for 30 minutes and (ii) is then drained by being hanged for 10 minutes. Unlike the CRC, it is possible to evaluate an amount of liquid retained between particles (gap) of the water absorbent resin.

(c) "AAP" (ERT442.2-02)

"AAP" is an abbreviation for Absorbency Against Pressure, and means water absorption capacity under load of the water absorbent resin. Specifically, "AAP" is water absorption capacity (unit; [g/g]) measured when 0.900 g of a water absorbent resin has swollen a large excess of a 0.9 mass % sodium chloride aqueous solution for 1 hour under a load of 2.06 kPa (0.3 psi, 21 [g/cm$^2$]). Note that Absorption Under Pressure in ERT442.2-02 is substantially identical with AAP. Moreover, measurement may be carried out under conditions where the load is changed to 4.83 kPa (0.7 psi, 50 [g/cm$^2$]).

Note that a water absorption capacity under load which is measured at 2.06 kPa is referred to as "AAP 0.3", and a water absorption capacity under load which is measured at 4.83 kPa is referred to as "AAP 0.7".

(d) "Ext" (ERT470.2-02)

"Ext" is an abbreviation for Extractables, and means a water soluble component (water soluble component amount) in the water absorbent resin. Specifically, "Ext" is a dissolved polymer amount (unit; mass %) measured when (i) 1.000 g of a water absorbent resin is added to 200 ml of a 0.9 mass % sodium chloride aqueous solution and (ii) stirring is carried out at 500 rpm for 16 hours. Note that the dissolved polymer amount is measured by pH titration.

(e) "PSD" (ERT420.2-02)

"PSD" is an abbreviation for Particle Size Distribution, and means a particle size distribution of the water absorbent resin which is measured by sieve classification. Moreover, a mass average particle diameter (D50) and a particle diameter distribution range of the water absorbent resin are measured according to a method similar to a method disclosed in the specification of European Patent No. 0349240, page 9, lines through 41, "(1) Average Particle Diameter and Distribution of Particle Diameter".

(f) "pH" (ERT400.2-02)

"pH" means pH of the water absorbent resin, and is defined by pH of a dispersion liquid containing a swollen gel, which dispersion liquid has been obtained by dispersing the water absorbent resin in a 0.9 mass % sodium chloride aqueous solution.

(1-5) "VDAUP"

"VDAUP" of the present invention is an abbreviation for Vertical Diffusion Absorbency Under Pressure, and means a vertical diffusion absorbency under load of the water absorbent resin. VDAUP is found to have a strong correlation with re-wet and absolute absorbency of a disposable diaper. Specifically, "VDAUP" is an amount of absorbed liquid (unit; [g]) obtained when 10.000 g of the water absorbent resin is swollen in a large excess of a 0.9 mass % sodium chloride aqueous solution for 1 hour under a load of 4.83 kPa (0.7 psi, 50 [g/cm$^2$]).

That is, VDAUP is different from the water absorption capacity under load (AAP) only in an amount of sample and load condition for measurement. Note that, unlike AAP that is defined by a mass ratio ([g/g]), VDAUP is defined by an absolute liquid amount ([g]).

Moreover, a basis weight of VDAUP is 11 times or more per unit area as high as that of AAP. Therefore, liquid diffusion property and liquid permeability between swollen gel layers are to greatly influence the method for measuring VDAUP, when an aqueous liquid is evenly absorbed by an entire sample. As such, a result of the VDAUP serves as an indicator for representing not only absorbency under load but also liquid diffusion property and liquid permeability of an actual absorbent body, in particular, an absorbent body in which a used ratio (i.e., concentration) of the water absorbent resin is high.

(1-6) Others

In this specification, a range "X to Y" means "X or more (higher) and Y or less (lower)". Moreover, "t (ton)", which is a unit of weight, means "metric ton", "weight" is synonymous with "mass", "wt %" is synonymous with "mass %", and "parts by weight" is synonymous with "parts by mass". Moreover, unless otherwise noted, "ppm" means "ppm by weight" or "ppm by mass". Further, " . . . acid (salt)" means " . . . acid and/or salt thereof", and "(meth) acrylic" means "acrylic and/or methacrylic".

[2] Method for Producing Particulate Water Absorbing Agent (2-1) Polymerization Step
(Monomer)

A water absorbent resin, which is used as a main component in the particulate water absorbing agent that is obtained by the production method of the present invention, is a polyacrylic acid (salt)-based water absorbent resin, and is a water-swelling and water-insoluble crosslinked polymer. This water-swelling and water-insoluble crosslinked polymer contains an acrylic acid (salt) as a monomer in a repeating unit (except for crosslinking agent later described), in an amount of preferably 30 mol % to 100 mol %, more preferably 50 mol % to 100 mol %, still more preferably 70 mol % to 100 mol %, and particularly preferably 90 mol % to 100 mol %, or substantially 100 mol %.

An acid group of the monomer is preferably neutralized. A neutralized salt is preferably monovalent salt, more preferably alkali metal salt or ammonium salt, still more preferably alkali metal salt, and particularly preferably, sodium salt. It is preferable that 0 mol % to 100 mol %, preferably 20 mol % to 100 mol %, more preferably 50 mol % to 99 mol %, and still more preferably 60 mol % to 90 mol % of the acid group be neutralized.

(Other Monomer and Crosslinking Agent)

According to the present invention, an unsaturated monomer (hereinafter, referred to as "other monomer") other than acrylic acid (salt) can be used in an amount of 0 mol % to 70 mol % of entire monomer components.

Examples of the "other monomer" encompass hydrophilic unsaturated monomers such as methacrylic acid, maleic acid (anhydride), fumaric acid, crotonic acid, itaconic acid, vinyl sulfonic acid, 2-(meth)acrylamide-2-methylpropane sulfonic acid, (meth)acryloxyalkane sulfonic acid, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethylene glycol (meth)acrylate, polyethylene glycol(meth)acrylate, and salts thereof.

The crosslinking agent that can be used in the present invention is not limited to a particular one, and can be, for example, the following compounds: (a) (i) compounds, each of which has at least two polymerizable double bonds per molecule, such as N,N'-methylenebisacrylamide, (poly)ethylene glycol di(meth)acrylate, (poly)propylene glycol di(meth)acrylate, (polyoxyethylene)trimethylolpropane tri (meth)acrylate, trimethylolpropanedi(meth)acrylate, polyethylene glycol di($\beta$-acryloyloxypropionate), trimethylolpropane tri($\beta$-acryloyloxypropionate), and poly(meth) allyloxyalkane; and (b) compounds each of which can form a covalent bond by reaction with a carboxyl group, such as (ii) polyglycidyl ethers such as ethylene glycol diglycidyl ether and (iii) polyols such as ethylene glycol, polyethylene glycol, glycerin, and sorbitol.

The crosslinking agent can be used solely or two or more crosslinking agents in combination. Note that, in a case where the crosslinking agent is used, it is preferable to use the compound that has at least two polymerizable double bonds per molecule, in consideration of an absorption performance etc. of a resultant particulate water absorbing agent. A used amount of the crosslinking agent is preferably 0 mol % to 5 mol %, and more preferably 0.001 mol % to 2 mol % relative to a monomer, from the viewpoint of physical properties.

According to the present invention, if needed, it is possible to add, to the monomer, preferably 5 mass % or lower, and more preferably 1 mass % or lower of a foaming agent, a deodorant agent, an antibacterial agent, a plasticizer, a perfume, a pigment, a dye, a hydrophilic short fiber, inorganic powder such as silicon dioxide and/or titanium oxide, polysaccharide such as starch and/or cellulose and a derivative thereof, a hydrophilic polymer such as polyvinyl alcohol, a thermoplastic resin such as polyethylene and/or polypropylene, a chain transfer agent such as hypophosphorous acid (salt), or the like.

Further, it is possible to have an arrangement in which a water absorbent resin and/or a water-soluble resin is present in the monomer at initiation of polymerization or in a water-containing gel-like crosslinked polymer (hereinafter, referred to as "hydrogel") during or after the polymerization. Specifically, it is possible to have an arrangement in which polysaccharide such as starch and/or cellulose and a derivative thereof, polyvinyl alcohol, or the like is present in an amount of preferably 0 mass % to 50 mass %, and more preferably 0.1 mass % to 30 mass %. A mixture with such a graft polymer or other polymer can be referred to as "water absorbent resin composition". Note, however, that, in the present invention, a mixture with such a graft polymer or other polymer is referred to as "water absorbent resin" or "polyacrylic acid (salt)-based water absorbent resin".

(Polymerization Method)

The polymerization carried out in the present invention is aqueous solution polymerization or reverse phase suspension polymerization, from the viewpoint of a water absorption performance of a resultant particulate water absorbing agent, easy polymerization control, and the like. These polymerizations can be carried out in an air atmosphere. However, from the viewpoint of improvement in coloration of the particulate water absorbing agent, the polymerizations are preferably carried out in an atmosphere of inert gas such as nitrogen or argon (for example, with an oxygen concentration of 1 volume % or lower). Further, it is preferable that dissolved oxygen in the monomer be sufficiently replaced by inert gas (so that an amount of the dissolved oxygen is, for example, less than 1 mg/L).

According to the present invention, the monomer is preferably used in a solution form obtained with water or with a mixed solvent of water and a hydrophilic solvent, and particularly preferably, in an aqueous solution form. That is, the polymerization step in the method for producing the particulate water absorbing agent according to the present invention is the step of polymerizing a water-soluble unsaturated monomer in which acrylic acid (salt) is contained as a main component. In this case, a monomer concentration is preferably 20 mass % to 80 mass %, more preferably 30 mass % to 70 mass %, and still more preferably 40 mass % to 60 mass %. Note that an excessively high monomer concentration tends to lower a water absorption capacity, and is therefore not preferable.

The aqueous solution polymerization is a method in which a monomer aqueous solution is polymerized without use of a dispersion solvent such as a hydrophobic organic solvent. This aqueous solution polymerization is a form of polymerization disclosed in, for example, U.S. Pat. Nos. 4,625,001, 4,873,299, 4,286,082, 4,973,632, 4,985,518, 5,124,416, 5,250,640, 5,264,495, 5,145,906, 5,380,808, and the like, European Patents Nos. 0811636, 0955086, 0922717, 1178059, 1711541, 1799721, and the like.

The reverse phase suspension polymerization is a method in which polymerization is carried out by suspending a monomer aqueous solution in a hydrophobic organic solvent. The reverse phase suspension polymerization is a form of polymerization disclosed in, for example, U.S. Pat. Nos. 4,093,776, 4,367,323, 4,446,261, 4,683,274, 5,244,735, and the like. Note that, in the polymerization of the present invention, the monomers, the crosslinking agents, the polymerization initiators, and other additives disclosed in the above Patent Literatures can also be used.

(Polymerization Initiator)

A polymerization initiator used in the present invention is selected as appropriate in accordance with a form of polymerization, and is not limited to a particular one. Examples of the polymerization initiator encompass a photolytic polymerization initiator, a pyrolytic polymerization initiator, a redox polymerization initiator, and the like. A used amount of the polymerization initiator is preferably 0.0001 mol % to 1 mol %, more preferably 0.001 mol % to 0.5 mol %, relative to the monomer.

Examples of the photolytic polymerization initiator encompass a benzoin derivative, a benzil derivative, an acetophenone derivative, a benzophenone derivative, an azo compound, and the like.

Examples of the pyrolytic polymerization initiator encompass persulfates such as sodium persulfate, potassium persulfate, and ammonium persulfate; peroxides such as hydrogen peroxide, t-butyl peroxide, and methyl ethyl ketone peroxide; azo compounds such as an azonitrile compound, an azoamidine compound, a cyclic azoamidine compound, an azoamide compound, an alkylazo compound, 2,2'-azobis(2-amidinopropane)dihydrochloride, and 2,2'-azobis[2-(2-imidazoline-2-yl)propane]dihydrochloride; and the like.

Examples of the redox polymerization initiator encompass a system using a combination of (i) the persulfate, the peroxide, or the like and (ii) a reducing compound such as L-ascorbic acid, or sodium hydrogen sulfite.

Alternatively, the photolytic polymerization initiator can be used in combination with the pyrolytic polymerization initiator.

(Surfactant, Dispersing Agent)

In the present invention, (i) a surfactant such as an anionic surfactant, a nonionic surfactant, a cationic surfactant, or an amphoteric surfactant and/or (ii) a dispersing agent can be used in polymerization. The surfactant and/or the dispersing agent are/is not limited to a particular one(s). Examples of the anionic surfactant encompass fatty acid sodiums such as mixed fatty acid sodium soap and sodium stearate, higher alcohol sodium sulfate, sodium alkyl sulfate, alkyl benzene sulfonate, and the like. Examples of the nonionic surfactant encompass polyoxyethylene alkyl ethers such as polyoxyethylene higher alcohol ether, sorbitan fatty acid ester, glycerin fatty acid ester, and the like. Examples of the cationic surfactant and the amphoteric surfactant encompass alkylamines, alkylbetaine, and the like.

Examples of the dispersing agent encompass ethyl cellulose ethyl hydroxyethyl cellulose and the like.

A used amount of the surfactant and/or the dispersing agent is determined as appropriate in accordance with a form of polymerization. In general, the used amount is preferably 0.0001 part by mass to 1 part by mass, more preferably 0.0005 part by mass to 0.5 part by mass, and still more preferably 0.001 part by mass to 0.1 part by mass, relative to 100 parts by mass of entire monomer components including polymerizable monomers and crosslinkable monomers.

(Organic Solvent in Reverse Phase Suspension Polymerization)

In a case where the reverse phase suspension polymerization is carried out, an organic solvent to be used is not limited to a particular one, provided that the organic solvent is poorly water soluble and inert with respect to polymerization. Examples of the organic solvent encompass aliphatic hydrocarbons such as n-pentane, n-hexane, n-heptane, and n-octane, alicyclic hydrocarbons such as cyclohexane and methylcyclohexane, aromatic hydrocarbons such as benzene, toluene, and xylene, and the like. Among these, n-hexane, n-heptane, and cyclohexane are particularly preferable, from the viewpoint of stability in industrial availability, quality, and the like. A used amount of the organic solvent is preferably 0.5 times to 10 times, more preferably 0.6 times to 5 times as large, by mass, as that of a polymerizable monomer solution.

(2-2) Gel-Grain Refining Step

The hydrogel obtained by the polymerization step can be directly dried (i.e., subjected to a drying step). However, in a case of aqueous solution polymerization, it is preferable that a hydrogel during or after polymerization is gel-crushed with use of a gel crusher (such as kneader or meat chopper, etc.) or the like, and the hydrogel thus grain-refined (hereinafter, referred to as "particulate hydrogel") is dried. In this case, grain refining of the hydrogel is carried out by a predetermined method so that a mass average particle diameter (D50) (defined by wet sieve classification) of the particulate hydrogel becomes preferably 0.1 mm to 50 mm, more preferably 0.2 mm to 10 mm, and still more preferably 0.5 mm to 5 mm.

Note that a form of the water absorbent resin used in the particulate water absorbing agent according to the present invention is not limited to a particular one and can be, for example, in an arbitrary form such as a granule form, a powder form, a flake form, or a fiber form. The grain refining can be carried out any of various methods such as a method in which gel-crushing is carried out with the use of a screw extruder having an arbitrarily-shaped porous structure.

(2-3) Drying Step

In the drying step, a hydrogel which has been obtained in the polymerization step or a particulate hydrogel which has been obtained in the gel-grain refining step is dried so as to obtain a dried polymer. A drying method here is not limited to a particular one and can be, for example, various drying methods such as drying by heating, hot air drying, drying under reduced pressure, fluidized-bed drying, infrared drying, microwave drying, drying with a drum dryer, dehydration by azeotropy with a hydrophobic organic solvent, and high humidity drying with hot moisture vapor.

Among these, a drying method carried out by contact with a gas is preferable, and a dew point of the gas to be used is preferably 40° C. to 100° C., and more preferably 50° C. to 90° C.

In the drying step of the present invention, a drying temperature is not limited to a particular one, and is, for example, preferably 50° C. to 300° C., and from the viewpoint of improvement in water absorption capacity, more preferably 100° C. to 250° C., still more preferably 120° C. to 230° C., and particularly preferably 150° C. to 200° C. Note that the "drying temperature" indicates a temperature of the gas to be contacted. Note that, in a case where the drying temperature is 100° C. or lower, the azeotropic dehydration or the drying under reduced pressure is preferable. Moreover, a drying time is determined as appropriate and is not limited to a particular time, and is, for example, preferably 10 seconds to 5 hours, and more preferably 1 minute to 2 hours.

In a case where the form of polymerization of the present invention is the aqueous solution polymerization, from the viewpoint of physical properties of an obtained particulate water absorbing agent, easy pulverization, and the like, a solid content (defined in (5-7) Moisture Content) of a dried polymer (water absorbent resin) after drying is preferably 80 mass % or higher, more preferably 85 mass % or higher, still more preferably 90 mass % or higher and particularly preferably 92 mass % to 98 mass %, and the dried polymer thus dried is then preferably further subjected to surface crosslinking.

In a case where the polymerization form of the present invention is the reverse phase suspension polymerization, a hydrogel obtained during or after polymerization can be dried by, for example, carrying out azeotropic dehydration in a state where the hydrogel is dispersed in an organic solvent of hydrocarbon or the like. The solid content after drying is 60 mass % or higher, preferably 70 mass % or higher, more preferably 80 mass % or higher, still more preferably 85 mass % or higher, further still more preferably 90 mass % or higher, particularly preferably 92 mass % to 98 mass %, and most preferably 93 mass % to 97 mass %.

In the reverse phase suspension polymerization, the surface crosslinking is carried out preferably during the drying step by the azeotropic dehydration (e.g., with the solid content of 60 mass % to 90 mass %). Note that, after the drying (i.e., after the drying step ends), the hydrogel can be separated from the organic solvent by decantation or evaporation, and can be then further dried if needed.

(2-4) Pulverizing Step, Classification Step

In this step, a dried polymer (i.e., dried hydrogel) obtained in the drying step is pulverized (pulverizing step) if needed, and is further classified (classification step) so as to control a particle size, so that water absorbent resin particles are obtained. The method for producing the particulate water absorbing agent according to the present invention more preferably includes the pulverizing step and the classification step between the drying step and the surface crosslinking step. That is, in the method for producing the particulate water absorbing agent according to the present invention, the pulverizing step and the classification step are not essential steps. However, it is preferable to carry out the pulverizing step, or both the pulverizing step and the classification step, after the drying step and before the surface crosslinking step (which will be described later). The pulverization and the classification can be carried out according to, for example, the method disclosed in International Publication No. 2004/69915.

The water absorbent resin particles (i.e., the water absorbent resin before surface crosslinking) are preferably controlled to have a particular range of particle size by the pulverizing step; or by both the pulverizing step and the classification step; and if needed, by further blending after classification, from the viewpoint of improvement in water absorption capacity under load (AAP) and vertical diffusion absorbency under load (VDAUP). The pulverizing step, or both the pulverizing step and the classification step can be, if needed, carried out with respect to the water absorbent resin after surface crosslinking and to the ultimate particulate water absorbing agent.

The pulverizing step can be carried out by, for example, pulverizing the dried polymer with a pulverizer. The pulverizer is not limited to a particular one and can be, for example, a roll crusher such as a roll mill, a hammer crusher such as a hammer mill, an impact crusher, a cutter mill, a turbo grinder, a ball mill, a flush mill, or the like. Among these, it is more preferable to use the roll mill for controlling particle size distribution.

In order to control the dried polymer, which has been thus pulverized, to have a particular particle size distribution, the classification step can be carried out by removing particles whose size is larger than a particular particle diameter with the use of a sieve having a particular mesh size. Moreover, particle sizes of the particles thus removed can be controlled to be in a particular particle diameter range by carrying out pulverization again.

A classifier used in the classification with a sieve is not limited to a particular one and can be, for example, a vibrating screen (such as an unbalanced weight driving type, a resonance type, a vibrating motor type, an electromagnetic type, or a circular vibrating type), an in-plane moving screen (such as a horizontal motion type, a horizontal circular-straight motion type, or a three dimensional circular motion type), a movable wire sieve, a forcible stirring sieve, a woven wire vibrating sieve, a wind power sieve, a sound wave sieve, or the like, and more preferably the vibrating screen or the in-plane moving screen.

A method for adjusting the particle size can be, for example, (i) a method in which the particle size is controlled to be in an intended range by controlling pulverizing conditions such as a clearance and a throughput of the crusher, a mesh size of a sieve used in the classification step, and the like, (ii) a method in which water absorbent resin particles having different particle sizes are mixed, or the like. In the adjusting method, it is necessary to control each of all the mass average particle diameter, the logarithmic standard deviation of particle size distribution, and contents of coarse particles and fine particles to fall within a predetermined range.

The classification step does not necessarily need to be carried out, provided that the water absorbent resin particles obtained through the pulverizing step satisfy the predetermined range. Meanwhile, in a case where the water absorbent resin particles obtained through the pulverizing step do not satisfy the predetermined range, it is possible to further carry out the classification step so that water absorbent resin particles obtained through the classification step satisfy the predetermined range.

The predetermined range is the mass average particle diameter (D50) which is 200 μm to 600 μm, preferably 250 μm to 550 μm, and more preferably 350 μm to 500 μm. Moreover, the logarithmic standard deviation (σζ) of particle size distribution is 0.20 to 0.50, preferably 0.25 to 0.45, and more preferably 0.30 to 0.35. Further, a ratio of coarse particles having a particle diameter of 850 µm or larger (defined by JIS-standard sieve) is preferably as low as possible, and is in general 0 mass % to 5 mass %, preferably 0 mass % to 3 mass %, and more preferably 0 mass % to 1 mass %, relative to a mass of the water absorbent resin particles. A ratio of fine particles having a particle diameter of smaller than 150 µm (defined by JIS-standard sieve) is also preferably as low as possible, and is in general 0 mass % to 5 mass %, preferably 0 mass % to 3 mass %, and more preferably 0 mass % to 1 mass %, relative to a mass of the water absorbent resin particles.

Furthermore, a bulk specific gravity (defined in U.S. Pat. No. 6,562,879) of water absorbent resin particles is preferably 0.30 to 0.90, more preferably 0.60 to 0.80, and still more preferably 0.65 to 0.75.

(2-5) Surface Crosslinking Step

In this step, surface crosslinking is carried out with respect to a dried polymer obtained through at least the polymerization step and the drying step, preferably to water absorbent resin particles obtained further through the pulverizing step, or both the pulverizing step and the classification step, in order to improve a water absorption capacity under load (AAP) of a resultant water absorbent resin. Note that the "surface crosslinking" indicates forming crosslinks on or in the vicinity of a surface of the dried polymer or the water absorbent resin particles. Moreover, "on or in the vicinity of a surface" means, in general, (i) a surface layer part having a thickness of several tens of micrometers or less or (ii) a surface layer part having a thickness of 1/10 or less of a whole thickness. Note, however, that the thickness is determined as appropriate in accordance with purposes.

The water absorbent resin used in the particulate water absorbing agent according to the present invention is obtained by surface crosslinking the dried polymer obtained through the polymerization step and the drying step; the dried polymer obtained through the polymerization step, the gel-grain refining step, and the drying step; the water absorbent resin particles obtained through the polymerization step, the gel-grain refining step, the drying step, and the pulverizing step; or the water absorbent resin particles obtained through the polymerization step, the gel-grain refining step, the drying step, the pulverizing step, and the classification step.

A method of the surface crosslinking is not limited to a particular one and can be, for example, (i) a method in which monomers are polymerized on a surface of the dried polymer or the water absorbent resin particles (ii) a method in which radical crosslinking is carried out on a surface of the dried polymer or the water absorbent resin particles with the use of a polymerization initiator (e.g., persulfate), or the like. Note, however, that it is particularly preferable to employ a method in which crosslinking is carried out on a surface of the dried polymer or the water absorbent resin particles with the use of a surface crosslinking agent. In this case, the surface crosslinking step includes a mixing step of mixing the dried polymer or the water absorbent resin particles with the surface crosslinking agent, a heat treating step of heat treating a mixture obtained in the mixing step, and, if needed, a cooling step of cooling the dried polymer or the water absorbent resin particles which have been subjected to the heat treating step.

(Surface Crosslinking Agent)

The surface crosslinking agent used in the present invention is not limited to a particular one and can be, for example, an oxazoline compound (see U.S. Pat. No. 6,297,319), a vinyl ether compound (see U.S. Pat. No. 6,372,852), an epoxy compound (see U.S. Pat. No. 625,488), an oxetane compound (see U.S. Pat. No. 6,809,158), a polyhydric alcohol compound (see U.S. Pat. No. 4,734,478), a polyamide polyamine-epihalo adduct (see U.S. Pat. Nos. 4,755, 562 and 4,824,901), a hydroxyacrylamide compound (see U.S. Pat. No. 6,239,230), an oxazolidinone compound (see U.S. Pat. No. 6,559,239), a bis or poly-oxazolidinone compound (see U.S. Pat. No. 6,472,478), a 2-oxotetrahydro-1, 3-oxazolidine compound (see U.S. Pat. No. 6,657,015), an alkylene carbonate compound (see U.S. Pat. No. 5,672,633), and the like, each of which is used solely or two or more of which are used in combination.

Further, it is possible to use the surface crosslinking agent in combination with water-soluble multivalent metal cation such as aluminum salt (see U.S. Pat. Nos. 6,605,673, and 6,620,899), or it is possible to use the surface crosslinking agent in combination with alkali metal salt (see US Patent Application Publication No. 2004/106745), organic acid or inorganic acid (see U.S. Pat. No. 5,610,208), or the like. Alternatively, the surface crosslinking can be polymerization of monomers on a surface of the water absorbent resin (see US Patent Application Publication No. 2005/48221).

Among these, it is preferable to use an organic surface crosslinking agent, in particular, a covalent bonding surface-crosslinking agent. Specifically, it is preferable to use at least one kind of a polyhydric alcohol compound, a polyvalent epoxy compound, a polyhydric amine compound or salt thereof, and an alkylene carbonate compound. In general, each of these compounds causes a surface to be hydrophilic, and therefore, allows efficient application of the production method of the present invention.

Examples of concrete surface crosslinking agents encompass polyhydric alcohol compounds such as (di, tri, tetra, poly)ethylene glycol, (di, poly)propylene glycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, di or triethanolamine, pentaerythritol, and sorbitol; epoxy compounds such as (poly)ethylene glycol diglycidyl ether, (di, poly) glycerol polyglycidyl ether, (di, poly)propylene glycol diglycidyl ether, and glycidol; polyvalent oxazoline compounds such as 1,2-ethylenebisoxazoline; alkylene carbonate compounds such as 1,3-dioxolane-2-one; mono-oxazolidinone compounds or multivalent oxazolidinone compounds such as 2-oxazolidinone; and oxetane compounds.

Among the above surface crosslinking agents, from the viewpoint of physical properties of a particulate water absorbing agent, it is preferable to use a dehydration reactive surface-crosslinking agent selected from among the polyhydric alcohol compound, the alkylene carbonate compound, the oxazolidinone compound, and the oxetane compound. In particular, it is preferable to use at least one selected from among the polyhydric alcohol compound, the alkylene carbonate compound, and the oxazolidinone compound, and if needed, other surface crosslinking agent(s). Note that, here, the dehydration reactive surface-crosslinking agent indicates a crosslinking agent for forming crosslinks by dehydration reaction with polyacrylic acid (salt) of a carboxyl group.

Surface crosslinking agents other than the above dehydration reactive surface-crosslinking agent can be, for example, an ion-reactive surface crosslinking agent such as multivalent metal salt, and a ring-opening-reactive surface crosslinking agent such as an epoxy compound crosslinking agent. These surface crosslinking agents can be used solely or in combination.

The ion reaction surface crosslinking agent can be a multivalent metal compound such as aluminum sulfate that contains a water-soluble multivalent metal cation.

A used amount of the surface crosslinking agent is preferably 0.01 part by mass to 10 parts by mass, and more preferably 0.5 part by mass to 5 parts by mass, relative to 100 parts by mass of the dried polymer or the water absorbent resin particles. In a case where the used amount of the surface crosslinking agent is less than 0.01 part by mass, a liquid permeability may decrease, and such an amount is therefore not preferable. On the other hand, in a case where the used amount of the surface crosslinking agent is more than 10 parts by mass, a water absorption capacity may extremely decrease, and such an amount is therefore not preferable.

Note that the surface crosslinking agent can be used solely or two or more of the surface crosslinking agents can be used in combination.

(Solvent)

When the dried polymer or the water absorbent resin particles are mixed with the surface crosslinking agent, the surface crosslinking agent can be solely mixed. Note, however, that it is preferable to mix the surface crosslinking agent in a solution form, and it is particularly preferable to use water as a solvent. In a case where a total used amount of water is 1 part by mass to 10 parts by mass relative to 100 parts by mass of the dried polymer or the water absorbent resin particles, a surface crosslinking agent aqueous solution sufficiently permeates the surface of the dried polymer or the water absorbent resin particles. Accordingly, multiple surface crosslinked layers are formed which have appropriate thickness and density.

When the surface crosslinking agent is mixed with the dried polymer or the water absorbent resin particles, if needed, a hydrophilic organic solvent can be used as a solvent. Examples of the hydrophilic organic solvent encompass lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and alkoxy polyethylene glycol; amides such as N,N-dimethylformamide; sulfoxides such as dimethyl sulfoxide; and the like. A used amount of the hydrophilic organic solvent varies depending on a type, a particle size, and the like of the dried polymer or the water absorbent resin particles, and is preferably 20 parts by mass or less, and more preferably 0.1 part by mass to 10 parts by mass, relative to 100 parts by mass of a solid content of the dried polymer or the water absorbent resin particles.

(Surface Crosslinking Method)

A method for mixing the dried polymer or the water absorbent resin particles with the surface crosslinking agent is not limited to a particular one, and is preferably a method in which a surface crosslinking agent, which is dissolved in water and/or a hydrophilic organic solvent, is mixed by direct spraying or dropping onto the dried polymer or the water absorbent resin particles.

A mixer used to mix the dried polymer or the water absorbent resin particles with the surface crosslinking agent preferably has a great mixing power so as to uniformly and reliably mix the dried polymer or the water absorbent resin particles with the surface crosslinking agent. The mixer is not limited to a particular one, and examples of the mixer encompass a cylindrical mixer, a double walled conical mixer, a V-shaped mixer, a ribbon mixer, a screw mixer, a flow furnace rotary disk type mixer, an airflow mixer, a double-arm kneader, an internal mixer, a pulverizing kneader, a rotary mixer, a screw extruder, a turbulizer, and the like.

When the surface crosslinking agent is mixed with the dried polymer or the water absorbent resin particles, temperatures of the dried polymer or the water absorbent resin particles, the surface crosslinking agent aqueous solution, and the mixture thereof are preferably 10° C. to 200° C., and more preferably 20° C. to 100° C. Moreover, a mixing time is preferably 1 second to 1 hour, and more preferably 5 seconds to 10 minutes.

The mixture of the dried polymer or the water absorbent resin particles and the surface crosslinking agent is preferably heated for causing a crosslinking reaction. A heating temperature can be selected as appropriate, and a heating medium temperature is preferably 150° C. to 250° C., and more preferably 180° C. to 210° C. A heating time is preferably 1 minute to 2 hours, and a preferable example of a combination of the heating temperature and the heating time is 0.1 to 1.5 hours at 180° C., 0.1 to 1 hour at 200° C., or the like.

When the mixture of the dried polymer or the water absorbent resin particles and the surface crosslinking agent is heated, the mixture can be heated in a still state or can be heated with the use of mixing means such as stirring. From the viewpoint of evenly heating the whole mixture, it is preferable to heat the mixture which is being mixed by stirring.

(2-6) Water-Soluble Non-Polymer Compound Adding Step

In the particulate water absorbing agent, the water-soluble non-polymer compound is preferably contained in the surface of the water absorbent resin. On this account, it is more preferable to carry out a water-soluble non-polymer compound adding step after the drying step. That is, the method for producing the particulate water absorbing agent according to the present invention preferably includes, after the drying step, the step of mixing a water-soluble non-polymer compound, preferably polyhydric alcohol and/or amino alcohol.

The water-soluble non-polymer compound adding step is preferably carried out, if needed, after the pulverizing step; or after the pulverizing step and the classification step. The water-soluble non-polymer compound adding step is more preferably carried out after or simultaneously with the surface crosslinking step. The water-soluble non-polymer compound adding step is still more preferably carried out simultaneously with the step of adding a multivalent metal cation. The water-soluble non-polymer compound adding step is particularly preferably carried out by adding an aqueous solution in which a multivalent metal cation and the water-soluble non-polymer compound exist together.

(Water-Soluble Non-Polymer Compound)

The water-soluble non-polymer compound is an organic compound, 1 g or more and preferably 10 g or more of which can be dissolved in 100 g of water at 25° C. and which has a molecular weight of 5000 or less.

The water-soluble non-polymer compound is preferably an organic compound that has a hydroxyl group and/or an amino group, more preferably a multifunctional organic compound in which a total number of a hydroxyl group(s) and an amino group(s) is 2 or more, and still more preferably a polyol compound, amino alcohol, a polyamine compound, or the like. Note that a compound can be used which is a derivative of the water-soluble non-polymer compound and which forms the water-soluble non-polymer compound by heat treating or hydrolysis. Such a compound is still more preferably an alkylene carbonate compound, a cyclic urethane compound, or the like.

Examples of the polyol compound encompass diol compounds such as ethylene glycol, 1,2-propanediol, 1,3-propanediol, 1,4-butanediol, 1,5-pentanediol, and 1,6-hexanediol; triol compounds such as glycerin and trimethylolpropane; and sugar alcohol compounds such as erythritol and xylitol. Examples of derivatives of these encompass alkylene carbonate compounds such as ethylene carbonate and propylene carbonate.

Examples of the amino alcohol encompass monoethanolamine, diethanolamine, n-propanolamine, and the like. Examples of derivatives of these encompass a cyclic urethane compound such as oxazolidinone.

Examples of the polyamine compound encompass ethylenediamine, 1,3-propanediamine, 1,2-propanediamine, and the like.

The water-soluble non-polymer compound is added, relative to 100 parts by mass of the water absorbent resin to which the water-soluble non-polymer compound is to be added, in preferably 0.001 part by mass to 10 parts by mass, more preferably 0.005 part by mass to 5 parts by mass, and still more preferably 0.01 part by mass to 3 parts by mass. Note that, in a case where a derivative of the water-soluble non-polymer compound is used, an amount of the derivative to be added is adjusted to fall within the above described amount of the water-soluble non-polymer compound to be added.

(2-7) Hydrophilic Polymer Compound Adding Step and Stabilizing Agent Adding Step The hydrophilic polymer compound adding step and the stabilizing agent adding step are preferably carried out (i) after the surface crosslinking step and (ii) not simultaneously with an inorganic element containing compound adding step which is carried out after surface crosslinking. Further, it is preferable to carry out the hydrophilic polymer compound adding step and the stabilizing agent adding step before the inorganic element containing compound adding step (that is, the step of adding multivalent metal cation and/or water-insoluble fine particles) after surface crosslinking.

The hydrophilic polymer compound adding step and the stabilizing agent adding step are more preferably carried out simultaneously, and are still more preferably carried out as the step of adding an aqueous solution that contains the hydrophilic polymer compound and the stabilizing agent.

In a case where the hydrophilic polymer compound adding step and the stabilizing agent adding step are carried out before the surface crosslinking step, in particular, simultaneously with the polymerization step or with preparation of monomers, the hydrophilic polymer compound and the stabilizing agent are retained inside the particulate water absorbing agent. As a result of this, the effect and the like of the present invention cannot be sufficiently brought about. For example, although a technique is known in which a polymerization inhibitor such as p-methoxyphenol or a hydrophilic graft component such as starch is added to monomers in polymerization, such a technique substantially cannot bring about the effect of the present invention for the reasons described above.

A difference between (a) the adding steps of the hydrophilic polymer compound and the stabilizing agent after the surface crosslinking step and (b) the adding steps of the hydrophilic polymer compound and the stabilizing agent before the surface crosslinking step can be confirmed as appropriate by, for example, (i) extracting a particle surface compound with the use of a non-swelling solvent (e.g., alcohol, mixed solvent of water and alcohol) with respect to the particulate water absorbing agent, (ii) checking content distribution for each particle size by utilizing an inverse proportion between a particle diameter and a surface area per unit mass, (iii) extraction from a substance obtained by grinding a surface of the particulate water absorbing agent, or the like.

The hydrophilic polymer compound is a polymer compound, 1 g or more of which can be dissolved in 100 g of water at 25° C. Moreover, the hydrophilic polymer compound is a generic term that is used to refer to a group of compounds that has a predetermined molecular weight or more and that encompass (i) compounds whose molecular weight is smaller than that of well-known polymers and whose number of repeating units, so-called oligomers, is approximately 100 or less and also (ii) compounds having a group which includes repeating units in a molecule.

A lower limit of the molecular weight is preferably 200 or more, more preferably 300 or more, and still more preferably 400 or more, while an upper limit of the molecular weight is preferably 10000 or less, preferably 5000 or less, and still more preferably 1000 or less. The number of repeating units is not limited to a particular one, provided that the molecular weight falls within the above described range.

A structure of the hydrophilic polymer compound can have a linear chain or a branched chain, and is more preferably a linear chain structure. The hydrophilic polymer compound still more preferably has a repeating structure in which repeating units are an ethoxyl group ($-CH_2-CH_2-O-$), more preferably has a structure in which the repeating structure forms a main chain, and particularly preferably 70 mass % or more of the repeating structure in the hydrophilic polymer compound. The hydrophilic polymer compound having the above described structure makes it possible to achieve a good water absorption performance and to reduce an amount of generated dust.

The hydrophilic polymer compound is preferably a compound that has a predetermined melting point or lower. The melting point is preferably 100° C. or lower, more preferably 70° C. or lower, still more preferably 50° C. or lower, and particularly preferably 30° C. or lower. A melting point in the above described range is preferable because the effect of the present invention can be advantageously brought about and it becomes easy to handle the hydrophilic polymer compound.

The hydrophilic polymer compound can be any of cationic, anionic, and nonionic compounds, and is preferably a nonionic compound. Specifically, examples of the hydrophilic polymer compound encompass polyvinyl alcohol, polyethylene oxide, polyethylene glycol, polypropylene glycol, polyacrylamide, polyacrylic acid, sodium polyacrylate, polyvinylamine, polyethyleneimine, methyl cellulose, carboxymethyl cellulose, hydroxyethyl cellulose, hydroxypropyl cellulose, dextrin, sodium alginate, starch, and the like. Among these, polyethylene glycol is preferable.

The hydrophilic polymer can be modified (e.g., alkyl-modified, ether-modified, carboxylalkyl-modified) if needed. Note, however, that the hydrophilic polymer compound is more preferably unmodified. For example, the polyethylene glycol can be a derivative such as methoxypolyethylene glycol but is more preferably unmodified polyethylene glycol.

A content of the hydrophilic polymer compound is preferably 0.01 part by mass or more, more preferably 0.05 part by mass or more, still more preferably 0.1 part by mass or more, and particularly preferably 0.15 part by mass or more, relative to 100 parts by mass of the water absorbent resin. Moreover, the content of the hydrophilic polymer compound is preferably 5.0 parts by mass or less, more preferably 4.0 parts by mass or less, still more preferably 3.0 parts by mass or less, and particularly preferably 2.5 parts by mass or less.

(Stabilizing Agent)

The stabilizing agent is selected from among a thioether-based stabilizing agent, a phosphoric acid-based stabilizing agent, and a phenol-based stabilizing agent, and is preferably a phenol-based stabilizing agent, and more preferably a t-butyl-phenol-based stabilizing agent.

The phenol-based stabilizing agent can be used in combination with a thioether-based stabilizing agent or a phosphoric acid-based stabilizing agent. Alternatively, two or more of phenol-based stabilizing agents can be used in combination.

Examples of the phenol-based stabilizing agent encompass n-octadecyl-3-(3,5-di-t-butyl-4-hydroxyphenyl)propionate, n-octadecyl-3-(3,5-di-t-butyl-4-hydroxyphenyl)acetate, n-octadecyl-3,5-di-t-butyl-4-hydroxybenzoate, n-hexyl-3,5-di-t-butyl-4-hydroxyphenyl benzoate, n-dodecyl-3,5-di-t-butyl-4-hydroxyphenyl benzoate, neododecyl-3-(3,5-di-t-butyl-4-hydroxyphenyl)propionate, dodecyl-β-(3,5-di-t-butyl-4-hydroxyphenyl)propionate, ethyl-α-(4-hydroxy-3,5-di-t-butylphenyl)isobutyrate, octadecyl-α-(4-hydroxy-3,5-di-t-butylphenyl)isobutyrate, octadecyl-α-(4-hydroxy-3,5-di-t-butyl-4-hydroxyphenyl)propionate, 2-(n-octylthio)ethyl-3,5-di-t-butyl-4-hydroxybenzoate, 2-(n-octylthio)ethyl-3,5-di-t-butyl-4-hydroxyphenylacetate, 2-(n-octadecylthio)ethyl-3,5-di-t-butyl-4-hydroxyphenylacetate, 2-(n-octadecylthio)ethyl-3,5-di-t-butyl-4-hydroxybenzoate, 2-(2-hydroxyethylthio)ethyl-3,5-di-t-butyl-4-hydroxybenzoate, diethyl glycol bis-(3,5-di-t-butyl-4-hydroxy-phenyl)propionate, 2-(n-octadecylthio)ethyl-3-(3,5-di-t-butyl-4-hydroxyphenyl)propionate, stearamide-N,N-bis-[ethylene-3-(3,5-di-t-butyl-4-hydroxyphenyl) propionate], n-butylimino-N,N-bis-[ethylene-3-(3,5-di-t-butyl-4-hydroxyphenyl)propionate], 2-(2-stearoyloxyethylthio)ethyl-3,5-di-t-butyl-4-hydroxybenzoate, 2-(2-stearoyloxyethylthio)ethyl-7-(3-methyl-5-t-butyl-4-hydroxyphenyl)heptanoate, 1,2-propylene glycol bis-[3-(3,5-di-t-butyl-4-hydroxyphenyl) propionate], ethylene glycol bis-[3-(3,5-di-t-butyl-4-hydroxyphenyl)propionate], neopentylglycol bis-[3-(3,5-di-t-butyl-4-hydroxyphenyl)propionate], ethyleneglycol bis-(3,5-di-t-butyl-4-hydroxyphenylacetate), glycerin-1-n-octadecanoate-2,3-bis-(3,5-di-t-butyl-4-hydroxyphenylacetate), pentaerythritol tetrakis-[3-(3',5'-di-t-butyl-4'-hydroxyphenyl)propionate], 1,1,1-trimethylolethanetris-[3-(3,5-di-t-butyl-4-hydroxyphenyl) propionate], sorbitolhexa-[3-(3,5-di-t-butyl-4-hydroxyphenyl)propionate], 2-hydroxyethyl-7-(3-methyl-5-t-butyl-4-hydroxyphenyl)propionate, 2-stearoyloxyethyl-7-(3-methyl-5-t-butyl-4-hydroxyphenyl)heptanoate, 1,6-n-hexanediolbis[(3',5'-di-t-butyl-4-hydroxyphenyl) propionate], pentaerythritol tetrakis(3,5-di-t-butyl-4-hydroxyhydrocinnamate), and 3,9-bis[1,1-dimethyl-2-[β-(3-t-butyl-4-hydroxy-5-methylphenyl)propionyloxy]ethyl]-2,4,8,10-tetraoxaspiro[5,5]-undecane.

Examples of the thioether-based stabilizing agent encompass pentaerythrityl tetrakis(3-lauryl thiopropionate), dilauryl-3,3'-thiodipropionate, dimyristyl-3,3'-thiodipropionate, and distearyl-3,3'-thiodipropionate.

Examples of the phosphoric acid-based stabilizing agent encompass tris(2,4-di-t-butylphenyl)phosphite, 2-[[2,4,8,10-tetrakis(1,1-dimethylethyl)dibenzo[d,f][1,3,2]dioxaphosphepin-6-yl]oxy]-N,N-bis[2-[[2,4,8,10-tetrakis(1,1dimethylethyl)dibenzo[d,f][1,3,2]dioxaphosphepin-6-yl]oxy]-ethyl]ethanamine, diphenyl tridecyl phosphite, triphenyl phosphite, 2,2-methylenebis(4,6-di-t-butylphenyl)octylphosphite, bis(2,6-di-t-butyl-4-methylphenyl)pentaerythritol diphosphite, distearylpentaerythritol diphosphite, and cyclic neopentanetetraylbis(2,6-di-t-butyl-4-methylphenyl) phosphite.

An amount of the stabilizing agent added is preferably 0.01 ppm by mass to 10 ppm by mass, more preferably 0.1 ppm by mass to 5 ppm by mass, and still more preferably 0.2 ppm by mass to 3 ppm by mass, relative to the water absorbent resin. In a case where the amount of the stabilizing agent added is excessively large, there may occurs a risk of bleed-out of the stabilizing agent or the like when a hygiene product such as a diaper is produced. Therefore, such an excessively large amount of the stabilizing agent is not preferable.

Moreover, it is more preferable to carry out heat treating after addition of the stabilizing agent, and a heating temperature is preferably 30° C. to 90° C., more preferably 40° C. to 80° C., and still more preferably 50° C. to 70° C. A heating time varies depending on the heating temperature, and is preferably 10 minutes to 180 minutes, more preferably 20 minutes to 150 minutes, still more preferably 30 minutes to 120 minutes, and particularly preferably 40 minutes to 90 minutes.

An amount of the stabilizing agent relative to the hydrophilic polymer compound is preferably 1 ppm by mass to 10000 ppm by mass, more preferably 10 ppm by mass to 5000 ppm by mass, still more preferably 30 ppm to 3000 ppm, and particularly preferably 40 ppm to 1500 ppm.

In order to evenly add the hydrophilic polymer compound and the stabilizing agent to the water absorbent resin, it is preferable to add a mixture of the hydrophilic polymer compound and the stabilizing agent, still more preferably a solution of the mixture, and particularly preferably an aqueous solution of the mixture, that is, an aqueous solution containing the hydrophilic polymer compound and the stabilizing agent. A concentration of the solution, in particular, a concentration of the aqueous solution is, in terms of a content of the hydrophilic polymer compound, preferably 4 mass % to 60 mass %, more preferably 5 mass % to 50 mass %, still more preferably 6 mass % to 40 mass %, further still more preferably 7 mass % to 30 mass %, and particularly preferably 8 mass % to 25 mass %, relative to a total weight of the aqueous solution, i.e., 100 mass % of the aqueous solution.

(2-8) Inorganic Element Containing Compound Adding Step after Surface Crosslinking Step The inorganic element containing compound, that is, the multivalent metal cation and/or the water-insoluble fine particles can be added after the drying step. The inorganic element containing compound is preferably added simultaneously with the surface crosslinking agent, and the inorganic element containing compound adding step is preferably carried out after the surface crosslinking step. In a case where the water-soluble non-polymer compound adding step is carried out after the surface crosslinking step, the inorganic element containing compound adding step can be carried out simultaneously with the water-soluble non-polymer compound adding step or after the water-soluble non-polymer compound adding step. The inorganic element containing compound adding step is preferably carried out separately from the hydrophilic polymer compound adding step, and more preferably carried out after the hydrophilic polymer compound adding step. Note that, in the present specification, the inorganic element containing compound adding step is also referred to as "step of adding a multivalent metal cation and/or water-insoluble fine particles".

(a) Multivalent Metal Cation Adding Step

A multivalent metal compound, which serves as a source of a multivalent metal cation that can be used in this multivalent metal cation adding step, is preferably a water-soluble compound. A valence of the cation is 2 or more (i.e., divalent or more), preferably 2 to 4 (i.e., divalent to tetravalent), and more preferably 3 (i.e., trivalent).

The water-soluble compound indicates a compound, 1 g or more, and preferably 10 g or more of which can be dissolved in 100 g of water (at 25° C.). The multivalent metal compound containing the multivalent metal cation as it is (i.e., mainly in a solid state) can be mixed with the water absorbent resin. Note, however, that it is preferable to mix an aqueous solution of the multivalent metal compound with the water absorbent resin, from the viewpoint of improvement in FSC.

A multivalent metal cationic element that can be used in the present invention is at least one metal selected from among main group metals and transition metals in groups 4 to 11, and is preferably one selected from among Mg, Ca, Ti, Zr, V, Cr, Mn, Fe, Co, Ni, Pd, Cu, Zn, Cd, and Al, more preferably Mg, Ca, Zn, and Al, and particularly preferably Al.

In the multivalent metal compound containing a multivalent metal cation, a counter anion is not limited in particular and can be organic or inorganic. Examples of such a multivalent metal compound encompass water-soluble aluminum salts such as aluminium acetate, aluminum lactate, aluminum acrylate, aluminium chloride, polyaluminum chloride, aluminum sulfate, aluminum nitrate, bis-potassium aluminum sulfate, and bis-sodium aluminum sulfate; water-soluble alkaline earth metal salts such as calcium chloride, calcium nitrate, magnesium chloride, magnesium sulfate, and magnesium nitrate; transition metal salts such as zinc chloride, zinc sulfate, zinc nitrate, copper sulfate, cobalt chloride, zirconium chloride, zirconium sulfate, and zirconium nitrate; and the like. Among these, an aluminum compound is particularly preferable, and further, aluminum sulfate is preferable. It is possible to most preferably use hydrated crystal powder such as aluminum sulfate tetradecahydrate to octadecahydrate.

In a case where an organic acid multivalent metal salt is used, an anion is preferably a base that corresponds to an acid such as anisic acid, benzoic acid, p-hydroxybenzoic acid, formic acid, valeric acid, citric acid, glycolic acid, glycerinic acid, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidino acetic acid, malic acid, isothionic acid, methylmaleic acid, adipic acid, itaconic acid, crotonic acid, oxalic acid, salicylic acid, gluconic acid, gallic acid, sorbic acid, or fatty acid such as stearic acid. Among these, tartrate and lactate are preferable, and lactate such as aluminum lactate or calcium lactate is the most preferable.

As to a method for mixing the multivalent metal cation, an aqueous solution containing the multivalent metal cation is mixed with the water absorbent resin. In particular, a concentration of the multivalent metal cation in the aqueous solution is 1 mass % to 60 mass %, further 10 mass % to 50 mass %. Furthermore, if needed, after mixing the multivalent metal cation, a resultant mixture can be heated at approximately 40° C. to 150° C., further 60° C. to 100° C. A used amount of water is preferably 0.1 part by mass to 5 parts by mass, and still more preferably 0.5 part by mass to 3 parts by mass, relative to 100 parts by mass of the water absorbent resin.

Still more preferably, a polyhydric alcohol compound and/or α-hydroxycarboxylic acid are/is also used in combination in the mixing. Note that the polyhydric alcohol compound and/or α-hydroxycarboxylic acid are/is selected as appropriate from among the above described compounds. A preferable used amount of the polyhydric alcohol compound and/or α-hydroxycarboxylic acid is (i) smaller than that of water and (ii) 0 part by mass to 4 parts by mass, 0.01 part by mass to 3 parts by mass, further 0.1 part by mass to 0.5 part by mass, relative to 100 parts by mass of the water absorbent resin.

A used amount of the multivalent metal compound (in terms of an amount of the multivalent metal cation) falls within preferably a range of 0.001 part by mass to 1 part by mass, more preferably a range of 0.005 part by mass to 0.5 part by mass, further still more preferably a range of 0.01 part by mass to 0.2 part by mass, and more preferably a range of 0.02 part by mass to 0.1 part by mass, relative to 100 parts by mass of the water absorbent resin powder.

In a case where the multivalent metal cation content in the particulate water absorbing agent is less than 0.001 part by mass relative to 100 parts by mass of the water absorbent resin, FSC may not be improved sufficiently. In a case where the content is more than 1 part by mass, AAP and VDAUP may significantly decrease.

(b) Water-Insoluble Fine Particles

The water-insoluble fine particles are not limited in particular, provided that, when the water absorbing agent comes in contact with an aqueous liquid, the water-insoluble fine particles inhibit particles of the water absorbing agent from cohering with one another so that the aqueous liquid flows well. Among these, water-insoluble inorganic fine powder is preferable, and inorganic fine particles such as bentonite, silicon dioxide, titanium oxide, and aluminum oxide, and further silicon fine particles are preferable because such inorganic fine particles improves an absorption capacity without load (FSC).

The water-insoluble fine particles have a volume average particle diameter of preferably 10 μm or smaller, more preferably 5 μm or smaller, still more preferably 1 μm or smaller, and particularly preferably 0.5 μm or smaller. Note that the volume average particle diameter can be calculated based on dynamic light scattering.

The water absorbent resin and the water-insoluble fine particles can be mixed by dry blending or the water absorbent resin can be mixed with use of a slurry (i.e., an aqueous dispersion) of the water-insoluble fine particles. It is preferable to employ the dry blending, and a mixer used in the dry blending is selected as appropriate.

A ratio of the water-insoluble fine particles relative to 100 parts by mass of the water absorbent resin is preferably 0.4 part by mass or less, more preferably 0.3 part by mass or less, still more preferably 0.2 part by mass or less, and particularly preferably 0.1 part by mass or less. A lower limit is preferably 0.001 part by mass or more, and more preferably 0.01 part by mass or more.

In a case where a content of the water-insoluble fine particles relative to 100 parts by mass of the water absorbent resin in the particulate water absorbing agent is less than 0.001 part by mass, improvement in FSC is insufficient. Moreover, in a case where the content is more than 0.4 part by mass, AAP and VDAUP may significantly decrease as a result of mixing.

(2-9) Chelating Agent Adding Step

The particulate water absorbing agent of the present invention preferably further contains a chelating agent. By thus containing the chelating agent, the particulate water absorbing agent can have an excellent urine resistance and color protection.

The chelating agent adding step can be carried out as an optional step, and can be carried out simultaneously with any of the above described steps. It is preferable to add the chelating agent to the monomer or the monomer solution in the polymerization step.

A form of addition of the chelating agent is not limited to a particular one. For example, the chelating agent can be added in a liquid form or a solid (powder) form as it is, or can be added as a solution that is obtained by dissolving the chelating agent in a solvent in advance. From the viewpoint of handleability, variation in added amount, and the like, it is preferable to add the chelating agent in the solution form.

The chelating agent is preferably a polymer chelating agent and/or a non-polymer chelating agent, and more preferably a non-polymer chelating agent, and a molecular weight or a mass average molecular weight is preferably 40 to 2000, more preferably 60 to 1000, and still more preferably 100 to 500.

Specifically, the chelating agent can be aminocarboxylic acid (salt), and the number of carboxyl groups thereof is preferably 2 to 20, more preferably 4 to 10, and particularly preferably 5 to 8.

In the present invention, a used amount of the chelating agent is preferably 0.00001 part by mass to 10 parts by mass, more preferably 0.0001 part by mass to 1 part by mass, and still more preferably 0.002 part by mass to 0.1 part by mass, relative to 100 parts by mass of the water absorbent resin.

In a case where the chelating agent content relative to 100 parts by mass of the water absorbent resin in the particulate water absorbing agent is more than 10 parts by mass, there occur problems, for example, that an effect that matches the content cannot be brought about (i.e., uneconomical) and an absorption performance deteriorates. On the other hand, in a case where the content is less than 0.00001 part by mass, a sufficient effect of addition of the chelating agent cannot be brought about.

(2-10) Deodorant Component Adding Step

It is possible to obtain a particulate water absorbing agent that is excellent in deodorizing property, by adding a deodorant component, preferably a plant component to the particulate water absorbing agent for the purpose of adding a deodorizing property. The deodorant component adding step can be carried out as an optional step, and is more preferably carried out after the surface crosslinking step.

The plant component is not limited to a particular one, and examples of the plant component encompass a compound that contains polyphenol, flavone, caffeine, tannin, tannic acid, nutgall, gallnut, gallic acid, or the like; Theaceae plants such as *Camellia*, *Eurya*, and *Ternstroemia*; Gramineae plants such as rice, bamboo grass, bamboo, corn, and barley, wheat and oat; Rubiaceae plants such as coffee; and the like. A form of the plant components is not limited to a particular one and can be, for example, an extract (essential oil) extracted from a plant, a plant itself, and plant residue and extract residue which are by-products generated in a production process in plant-processing industry and in food-processing industry.

A used amount of the plant component in the present invention is 0 part by mass to 10 parts by mass, preferably 0.001 part by mass to 5 parts by mass, and still more preferably 0.002 part by mass to 3 parts by mass, relative to 100 parts by mass of the water absorbent resin. The used amount within the above described range makes it possible to achieve the deodorizing property.

(2-11) Granulating Step

According to the present invention, it is preferable to granulate the water absorbent resin. In granulation, a used amount of water varies depending on a moisture content of the water absorbent resin, and is, in general, preferably 0.5 part by mass to 20 parts by mass, and more preferably 0.5 part by mass to 10 parts by mass, relative to 100 parts by mass of a solid content in the water absorbent resin. In addition to water, it is possible to use a hydrophilic organic solvent.

(2-12) Surfactant Adding Step

In the method for producing the particulate water absorbing agent according to the present invention, it is preferable to add a surfactant after the drying step. The wording "add a surfactant after the drying step" means neither (i) adding a surfactant to a monomer solution nor (ii) adding a surfactant in the polymerization step. The surfactant can be added simultaneously with the surface crosslinking agent.

An amount of the surfactant to be added is more than 0 part by mass and 10 parts by mass or less, preferably more than 0 part by mass and 5 parts by mass or less, and more preferably more than 0 part by mass and 1 part by mass or less, relative to 100 parts by mass of the water absorbent resin to which the surfactant has not yet been added. The surfactant to be used in this surfactant adding step is disclosed in U.S. Pat. No. 7,473,739, etc.

(2-13) Water Adding Step

In the method for producing the particulate water absorbing agent according to the present invention, it is preferable to add, to the water absorbent resin after the drying step, water in 1 mass % to 15 mass %. This step is more preferably the step of obtaining a water absorbing agent that contains water by 5 mass % to 10 mass %. This step means that is it possible to additionally add only water for obtaining the water absorbing agent that has a moisture content of 5 mass % to 10 mass %.

As described above, the particulate water absorbing agent according to the present invention can be obtained by carrying out at least the polymerization step of polymerizing the water-soluble unsaturated monomer that contains acrylic acid (salt) as a main component, the drying step, the surface crosslinking step, and the hydrophilic polymer compound adding step and the stabilizing agent adding step after the surface crosslinking step, and carrying out, as necessary, at least one step selected from among the gel-grain refining step, the pulverizing step or both the pulverizing step and the classification step, the water-soluble non-polymer compound adding step, the step of adding a multivalent metal cation and/or water-insoluble fine particles, the surfactant adding step, and the step of adding 1 mass % to 15 mass % of water relative to the water absorbing agent.

[2'] Method for Evaluating Increase Over Time in Dust Amount of Particulate Water Absorbing Agent A method of the present invention for evaluating an increase over time in dust amount of the particulate water absorbing agent is a method for evaluating an increase over time in dust amount of the particulate water absorbing agent, based on a dust amount after heat treatment in which the particulate water absorbing agent is stored in a sealed container at 60° C. for 3 weeks.

That is, the method includes (i) the step of subjecting the particulate water absorbing agent to heat treatment by storing the particulate water absorbing agent at 60° C. for 3 weeks in a sealed container and (ii) the step of evaluating an increase over time in dust amount of the particulate water absorbing agent by measuring a dust amount after the heat treatment.

According to the method, as described later in Examples, it is possible to accurately predict, in 3 weeks after production, a dust amount that would be generated when the particulate water absorbing agent is stored for a long time (e.g., 3 months) after the production.

Specifically, a method described later in (5-11) can be employed, but the method is not limited to this. For example, in the method described in (5-11), at least 100 g of the particulate water absorbing agent is necessary for measuring the dust amount after the heat treatment, and therefore an amount of the particulate water absorbing agent to be put in the container may be at least 150 g, and an upper limit of the amount may be 300 g. If the amount is too large, the particulate water absorbing agent may not be cooled down to a room temperature even 2 hours after the container is taken out from a thermostat.

According to the method described in (5-11), a material of the container is not limited to polypropylene, provided that the material can be sealed and is not deformed or cracked by the heat treatment. Note, however, that iron and copper are not preferable because iron and copper may deteriorate the water absorbing agent.

According to the method described in (5-11), the container preferably has an internal volume with which an approximate filling rate of the particulate water absorbing agent becomes preferably 30% to 70%, and more preferably 40% to 60%. For example, in a case where 200 g of the particulate water absorbing agent is put in the container, in general, the internal volume is preferably 500 ml to 600 ml.

[3] Particulate Water Absorbing Agent and Physical Properties Thereof

The particulate water absorbing agent according to the present invention is a particulate water absorbing agent which contains (i) a polyacrylic acid (salt)-based water absorbent resin as a main component, (ii) a hydrophilic polymer compound, and (iii) a stabilizing agent, and the polyacrylic acid (salt)-based water absorbent resin is a surface crosslinked polyacrylic acid (salt)-based water absorbent resin. The "polyacrylic acid (salt)-based water absorbent resin", the "main component", and the "hydrophilic polymer compound and stabilizing agent" have already been described above.

In the particulate water absorbing agent according to the present invention, it is preferable that dust after mechanical treatment is in an amount of less than 30 mg/kg and dust after heat treatment at 60° C. for 3 weeks is in an amount of less than 30 mg/kg.

The mechanical treatment is a treatment that is carried out according to a method described later in (5-12). The dust amount after the treatment is preferably 30 mg/kg or less, more preferably 25 mg/kg or less, still more preferably 20 mg/kg or less, further still more preferably 15 mg/kg or less, and particularly preferably 10 mg/kg. Note that a lower limit is 0 mg/kg.

The heat treatment is a treatment carried out according to a method described later in (5-11), and the heat treatment makes it possible to evaluate, in a short period of time, an amount of dust that would be generated after long-term storage. Specifically, the amount is a dust amount after storage at 60° C. for 3 weeks in the sealed container. The dust amount after the heat treatment is preferably 30 mg/kg or less, more preferably 28 mg/kg or less, still more preferably 25 mg/kg or less, and particularly preferably 20 mg/kg or less. Note that a lower limit is 0 mg/kg.

Note that two kinds of dust amounts as described above increase over time after the production, even for the same particulate water absorbing agent. Accordingly, in a case where the dust amounts become out of the above described respective ranges after a considerably long time has elapsed, the effect of the present invention cannot be brought about.

The surface crosslinked polyacrylic acid (salt)-based water absorbent resin can be obtained by surface crosslinking (i) a dried polymer that has been obtained through the polymerization step and the drying step; (ii) a dried polymer that has been obtained through the polymerization step, the gel-grain refining step, and the drying step; (iii) water absorbent resin particles that have been obtained through the polymerization step, the gel-grain refining step, the drying step, and the pulverizing step; or water absorbent resin particles that have been obtained through the polymerization step, the gel-grain refining step, the drying step, the pulverizing step, and the classification step.

In the particulate water absorbing agent according to the present invention, a content of the hydrophilic polymer compound is preferably 0.01 part by mass to 5.0 parts by mass relative to 100 parts by mass of the polyacrylic acid (salt)-based water absorbent resin. Moreover, a content of the stabilizing agent is preferably 0.01 ppm by mass to 10 ppm by mass relative to the polyacrylic acid (salt)-based water absorbent resin.

The hydrophilic polymer compound has already been described above in (2-7). As described in the above (2-7), the content of the hydrophilic polymer compound is preferably 0.01 part by mass or more, more preferably 0.05 part by mass or more, still more preferably 0.1 part by mass or more, and particularly preferably 0.15 part by mass or more. Moreover, the content of the hydrophilic polymer compound is preferably 5.0 parts by mass or less, more preferably 4.0 parts by mass or less, still more preferably 3.0 parts by mass or less, and particularly preferably 2.5 parts by mass or less, relative to 100 parts by mass of the polyacrylic acid (salt)-based water absorbent resin.

The stabilizing agent also has already been described above in (2-7). As described in the above (2-7), an amount of the stabilizing agent to be added is preferably 0.01 ppm by mass to 10 ppm by mass relative to 100 parts by mass of the polyacrylic acid (salt)-based water absorbent resin. That is, in the particulate water absorbing agent according to the present invention, a content of the stabilizing agent is preferably 0.01 ppm by mass to 10 ppm by mass relative to the polyacrylic acid (salt)-based water absorbent resin. Moreover, the content is more preferably 0.1 ppm by mass to 5 ppm by mass, and still more preferably 0.2 ppm by mass to 3 ppm by mass.

The particulate water absorbing agent according to the present invention preferably further includes a water-soluble non-polymer compound. The water-soluble non-polymer compound has already been described above in (2-6). As described in the above (2-6), a content of the water-soluble non-polymer compound is preferably 0.001 part by mass to 10 parts by mass, more preferably 0.005 part by mass to 5 parts by mass, and still more preferably 0.01 part by mass to 3 parts by mass, relative to 100 parts by mass of the polyacrylic acid (salt)-based water absorbent resin.

The particulate water absorbing agent according to the present invention preferably further includes a multivalent metal cation. The multivalent metal cation has already been described above in (2-8). As described in the above (2-8), a content of the multivalent metal cation is preferably 0.001 part by mass to 1 part by mass, more preferably 0.005 part by mass to 0.5 part by mass, still more preferably 0.01 part by mass to 0.2 part by mass, relative to 100 parts by mass of the polyacrylic acid (salt)-based water absorbent resin.

The particulate water absorbing agent according to the present invention preferably further includes a surfactant. The surfactant has already been described above in (2-12). As described in the above (2-12), a content of the surfactant is more than 0 part by mass and 10 parts by mass or less, preferably more than 0 part by mass and 5 parts by mass or less, and more preferably more than 0 part by mass and 1 part by mass or less, relative to 100 parts by mass of the water absorbent resin to which the surfactant has not been added. The surfactant and the like to be used in this case are disclosed in U.S. Pat. No. 7,473,739 etc.

In the particulate water absorbing agent according to the present invention, a moisture content is preferably 1 mass % to 15 mass %. The moisture content is more preferably 5 mass % to 10 mass %. The moisture content is a mass ratio of water which is contained in 100 mass % of the particulate water absorbing agent. The moisture content of the particulate water absorbing agent according to the present invention can be confirmed by, for example, a method later described in (5-7).

A method for producing the particulate water absorbing agent according to the present invention whose moisture content falls within the above described range can be the method described in above (2-13).

In the particulate water absorbing agent according to the present invention, a vertical diffusion absorbency under load is preferably 30 g or higher. As described above in (3-3), the vertical diffusion absorbency under load is 30 g to 80 g, 35 g to 75 g, 40 g to 70 g, and 40 g to 65 g, in an ascending preference order.

The present invention (for example, the above described method for producing a particulate water absorbing agent) provides the novel particulate water absorbing agent which (i) contains the surface crosslinked polyacrylic acid (salt)-based water absorbent resin as a main component and (ii) achieves physical properties described below. Note that respective methods for measuring the physical properties are described in Examples below.

(3-1) Water Absorption Capacity without Load after Hanging (FSC)

The water absorption capacity without load after hanging (FSC) of the particulate water absorbing agent according to the present invention is 48 [g/g] to 65 [g/g], preferably 50 [g/g] to 63 [g/g], more preferably 51 [g/g] to 60 [g/g], and still more preferably 51 [g/g] to 58 [g/g]. In a case where the water absorption capacity without load after hanging (FSC) is less than 48 [g/g], it is not possible to obtain an excellent absolute absorbency when the particulate water absorbing agent is used for an absorbent article (particularly, a disposable diaper). Therefore, an FSC less than 48 [g/g] is not preferable.

(3-2) Water Absorption Capacity under Load (AAP—4.83 kPa)

The water absorption capacity under load (AAP—4.83 kPa) of the particulate water absorbing agent according to the present invention is 19 [g/g] to 30 [g/g], preferably 20 [g/g] to 30 [g/g], and more preferably 20 [g/g] to 27 [g/g]. In a case where the water absorption capacity under load (AAP—4.83 kPa) is less than 19 [g/g], a returned liquid amount (Re-Wet) becomes larger when the particulate water absorbing agent is used for an absorbent article (particularly, for a disposable diaper). Therefore, the water absorption capacity under load less than 19 [g/g] is not preferable.

(3-3) Vertical Diffusion Absorbency Under Load (VDAUP)

The vertical diffusion absorbency under load (VDAUP) of the particulate water absorbing agent according to the present invention is 30 g to 80 g, preferably 35 g to 75 g, more preferably 40 g to 70 g, and still more preferably 40 g to 65 g. In a case where the vertical diffusion absorbency under load (VDAUP) is less than 30 g, a returned liquid amount (Re-Wet) becomes larger when the particulate water absorbing agent is used for an absorbent article (particularly, for a disposable diaper). Therefore, the vertical diffusion absorbency under load (VDAUP) less than 30 g is not preferable.

(3-4) Water Absorption Capacity without Load (CRC)

The water absorption capacity without load (CRC) of the particulate water absorbing agent according to the present invention is preferably 30 [g/g] or higher, more preferably 31 [g/g] or higher, and still more preferably 32 [g/g] or higher. In a case where the above water absorption capacity without load (CRC) is less than 30 [g/g], a high physical property may not be exhibited when the particulate water absorbing agent is used for an absorbent article such as a disposable diaper. Note that although a higher upper limit of the water absorption capacity without load (CRC) is more preferable, a water absorption capacity without load of approximately 45 [g/g] in general, further approximately 40 [g/g], or in particular, approximately 38 [g/g] is sufficient, from the viewpoint of a balance with other physical properties and production costs.

(3-5) Evaluation of Dust Amount after Heat Treatment

According the evaluation method of the present invention, evaluation is performed based on a dust amount of the particulate water absorbing agent after storage of this particulate water absorbing agent at 60° C. for 3 weeks in a sealed container. The dust amount after the treatment is preferably 30 mg/kg or less, more preferably 28 mg/kg or less, still more preferably 25 mg/kg or less, and particularly preferably 20 mg/kg or less. Note that measurement itself of the dust amount is carried out according to a method described in (5-10).

(3-6) Other Physical Properties

The water absorption capacity under load (AAP—2.06 kPa) of the particulate water absorbing agent according to the present invention is preferably 25 [g/g] or higher, and more preferably 30 [g/g] or higher. In a case where the water absorption capacity under load (AAP—2.06 kPa) is less than 25 [g/g], the effect of the present invention may not be brought about. Note that although a higher upper limit of the water absorption capacity under load (AAP—2.06 kPa) is more preferable, a water absorption capacity under load of approximately 40 [g/g], or in particular, approximately 38 [g/g] is sufficient from the viewpoint of a balance with other physical properties and production costs.

The form of the particulate water absorbing agent according to the present invention is not limited to a particular one, provided that the particulate water absorbing agent has a particle form. The particulate water absorbing agent may have, for example, a spherical form, a substantially spherical form, an irregularly crushed piece form (that is, a crushed substance), a bar form, a polygonal form, a sausage form (for example, U.S. Pat. No. 4,973,632 etc.), a wrinkled particle form (for example, U.S. Pat. No. 5,744,564 etc.), or the like. Such particles can be primary particles (single particles), granulated particles, or a mixture thereof. Further, these particles can be expanded porous particles. Among these particles, irregularly crushed primary particles or granulated particles are preferable.

The mass average particle diameter (D50) of the particulate water absorbing agent is preferably 200 µm to 600 µm, more preferably 250 µm to 550 µm, and still more preferably 350 µm to 500 µm.

Further, the logarithmic standard deviation (σζ) of the particle size distribution is preferably 0.20 to 0.50, more preferably 0.25 to 0.45, and still more preferably 0.30 to 0.35.

Further, a smaller ratio of coarse particles having a mass average particle diameter (D50) of 850 µm or more (defined by JIS Standard sieve) is more preferable. A ratio of such coarse particles is 0 mass % to 5 mass % in general, preferably 0 mass % to 3 mass %, and more preferably 0 mass % to 1 mass %.

Furthermore, a smaller ratio of fine particles having a mass average particle diameter (D50) of less than 150 µm (defined by JIS Standard sieve) is more preferable. A ratio of such fine particles is 0 mass % to 5 mass % in general, preferably 0 mass % to 3 mass %, and more preferably 0 mass % to 1 mass %.

Further, a bulk specific gravity (defined in U.S. Pat. No. 6,562,879) of the water absorbent resin particle is preferably 0.30 to 0.90, more preferably 0.60 to 0.80, and still more preferably 0.65 to 0.75.

In consideration of the returned liquid amount in a case where the particulate water absorbing agent is used for a diaper or the like, the surface tension (described in Pamphlet of International Publication No. WO2005/075070) of the particulate water absorbing agent is preferably 50 mN/m or higher, more preferably 60 mN/m or higher, still more preferably 65 mN/m or higher, and particularly preferably 70 mN/m or higher. In general, an upper limit of the surface tension is approximately 73 mN/m. The surface tension can be controlled by controlling a used amount of a surfactant or by not using a surfactant. In a case where the hydrophilic polymer compound used in the present application is surface-active (for example, in the case of long-chain alkyl-modified polyethylene glycol), the surface tension can be controlled as appropriate by controlling an amount of the hydrophilic polymer compound to be added.

The above-described particle size (mass average particle diameter (D50), logarithmic standard deviation (σζ), ratio of coarse particles or fine particles) and the bulk specific gravity are suitably applied not only to the water absorbent resin particle but also to a surface-crosslinked water absorbent resin and an ultimate particulate water absorbing agent. In a case where the particle size is out of the above-described range, deterioration in water absorption capacity under load (AAP) and vertical diffusion absorbency under load (VDAUP) and increase in returned liquid amount (Re-Wet) in a disposable diaper are observed. Therefore, such a particle size is not preferable.

Further, the moisture content is preferably 1 mass % to 15 mass %, more preferably 3 mass % to 10 mass %, and particularly preferably 5 mass % to 10 mass %. Such a moisture content can be obtained by addition of water to a finished particulate water absorbing agent, regulation of a heating temperature and/or heating period in the above steps, and regulation of an amount of water used in various addition steps.

[4] Application Etc. Of Particulate Water Absorbing Agent

Applications of the particulate water absorbing agent according to the present invention are not limited in particular. However, the particulate water absorbing agent is preferably formed into an absorbent body and then used for an absorbent articles (for example, disposable diapers) as ultimate consumable goods.

(4-1) Absorbent Body

The absorbent body in the present invention is obtained by forming the particulate water absorbing agent into a sheet form, a web form, a cylindrical form, or the like. Note that the "absorbent body" means a water absorbing material obtained by forming, into a shape, the particulate water absorbing agent and a hydrophilic fiber such as pulp as main components.

Further, the particulate water absorbing agent of the present invention has an excellent liquid permeability (vertical diffusion absorbency under load/VDAUP). Therefore, when the particulate water absorbing agent is used for the absorbent body, a content of the hydrophilic fiber can be reduced. Accordingly, even when a core concentration is arranged to be 40 mass % or higher, an excellent liquid diffusion property is obtained. This makes it possible to quickly absorb and diffuse a large amount of aqueous liquid at once. Furthermore, the absorption performance can be maintained for a long time, and additionally, there occurs no return of absorbed aqueous liquid. As described above, use of the particulate water absorbing agent of the present invention makes it possible to actually reduce a thickness of the absorbent body (particularly, a disposable diaper).

(4-2) Absorbent Article

The absorbent article in the present invention is ultimate consumable goods that are intended for water absorption, gelatification, moisture retention, water stop, moisture absorption, and the like. The ultimate consumable goods are absorbent articles including the absorbent body, a front surface sheet having liquid permeability, and a liquid-impermeable back surface sheet. Specifically, examples of the absorbent particles encompass a disposable diaper, an incontinence pad, a sanitary napkin, etc., and particularly preferably a disposable diaper. Note that the absorbent article can also be applied to other hygiene materials.

The present invention can be also configured as follows.

The particulate water absorbing agent of the present invention includes: a polyacrylic acid (salt)-based water absorbent resin as a main component; a hydrophilic polymer compound; and a stabilizing agent, wherein a dust amount after mechanical treatment is 30 mg/kg or less, and a dust amount after heat treatment at 60° C. for 3 weeks is 30 mg/kg or less.

The particulate water absorbing agent of the present invention is configured preferably such that the water absorbent resin is surface-crosslinked.

The particulate water absorbing agent of the present invention is configured preferably such that a content of the hydrophilic polymer compound is 0.01 part by mass to 5.0 parts by mass relative to 100 parts by mass of the water absorbent resin.

The particulate water absorbing agent of the present invention is configured preferably such that an added amount of the stabilizing agent is 0.01 ppm by mass to 10 ppm by mass relative to the water absorbent resin.

Preferably, the particulate water absorbing agent of the present invention further includes a water-soluble non-polymer compound.

Preferably, the particulate water absorbing agent of the present invention further includes a multivalent metal cation.

Preferably, the particulate water absorbing agent of the present invention further includes a surfactant.

The particulate water absorbing agent of the present invention is configured preferably such that a moisture content is 1 mass % to 15 mass %.

The particulate water absorbing agent of the present invention is configured preferably such that a vertical diffusion absorbency under load is 30 g or higher.

A method for producing a particulate water absorbing agent of the present invention including a polyacrylic acid (salt)-based water absorbent resin as a main component, the method including a polymerization step of a water-soluble unsaturated monomer containing an acrylic acid (salt) as a main component, a drying step and a surface crosslinking step, the method further includes the steps of: (a) adding a hydrophilic polymer compound; and (b) adding a stabilizing agent, the steps (a) and (b) being carried out after the surface crosslinking step.

The method of the present invention for producing the particulate water absorbing agent is configured preferably such that the steps (a) and (b) are simultaneously carried out.

The method of the present invention for producing the particulate water absorbing agent is configured preferably such that the steps (a) and (b) are carried out by adding an aqueous solution containing the hydrophilic polymer compound and the stabilizing agent.

Preferably, the method of the present invention for producing the particulate water absorbing agent further includes the step of mixing a water-soluble non-polymer compound after the drying step.

Preferably, the method of the present invention for producing the particulate water absorbing agent further includes: after the drying step and before the surface crosslinking step, a pulverizing/classification step.

Preferably, the method of the present invention for producing the particulate water absorbing agent further includes the step of adding a multivalent metal cation and/or a water-insoluble fine particle after the drying step.

Preferably, the method of the present invention for producing the particulate water absorbing agent further includes the step of adding a surfactant after the drying step.

Preferably, the method of the present invention for producing the particulate water absorbing agent further includes the step of adding water in an amount of 1 mass % to 15 mass % relative to a water absorbing agent after the drying step.

A method of the present invention for evaluating an increase over time in dust amount of a particulate water absorbing agent evaluates the increase over time in dust amount of the particulate water absorbing agent based on a dust amount of the particulate water absorbing agent having been subjected to heat treatment in which the particulate water absorbing agent is stored at 60° C. for 3 weeks in a sealed container.

EXAMPLES

[5] Examples

The following more specifically discusses the present invention by providing Examples and Comparative Examples. Note that all electronic apparatuses etc. used in Examples and Comparative Examples were used at 100V and 60 Hz. Further, unless noted otherwise, physical properties were measured at a room temperature (23° C.±2° C.) and a relative humidity of 50% RH.

For convenience, "mass %" may be written as "wt %" while "liter" may be written as "L". Further, in the present specification, "0.90 mass % sodium chloride aqueous solution" are, in some cases, referred to as "physiological saline solution", and these terms are understood as identical. Furthermore, for convenience, the term "particulate water absorbing agent" used in (5-1) to (5-13) is read as "water absorbent resin particle", "water absorbent resin" or the like in a case where the "water absorbent resin particle", "water absorbent resin" or the like was measured.

(5-1) Water Absorption Capacity without Load (CRC)

The water absorption capacity without load (CRC) of the particulate water absorbing agent according to the present invention was measured according to ERT441.2-02.

That is, 0.200 g (W0 [g] in mass) of the particulate water-absorbing agent was weighed, put evenly in a non-woven fabric bag (60 mm×85 mm) and sealed by heat. Then, the non-woven fabric bag was soaked in 500 ml of a 0.9 wt % sodium chloride aqueous solution whose temperature was controlled to 23° C.±2° C. After 30 minutes, the non-woven fabric bag was taken out and subjected to draining at 250G for 3 minutes by used of a centrifugal separator (manufactured by KOKUSAN Co., Ltd., model: H-122). Thereafter, a mass (W1 [g]) of the bag was measured.

The same operation was carried out for a bag where no particulate water absorbing agent was put in and a mass (W2 [g]) of this bag was measured. The water absorption capacity without load (CRC) was calculated by the following Mathematical Formula 1 by using thus obtained W0 [g], W1 [g], and W2 [g].

$$CRC\ [g/g] = \{(W1-W2)/W0\} - 1 \qquad [\text{Math. 1}]$$

(5-2) Water Absorption Capacity without Load after Hanging (FSC)

The water absorption capacity without load after hanging (FSC) of the particulate water absorbing agent according to the present invention was measured according to ERT440.2-02.

That is, 0.200 g (W3 [g] in mass) of the particulate water absorbing agent was weighed, put evenly in a non-woven fabric bag (60 mm×85 mm) and sealed by heat. Then, the non-woven fabric bag was soaked in 500 ml of a 0.9 wt % sodium chloride aqueous solution whose temperature was controlled to 23° C.±2° C. After 30 minutes, the non-woven fabric bag was taken out and hung for 10 minutes for draining. Thereafter, a mass (W4 [g]) of the bag was measured.

The same operation was carried out for a bag where no particulate water absorbing agent was put in and a mass of this bag (W5 [g]) was measured. The water absorption capacity without load after hanging (FSC) was calculated by the following Mathematical Formula 2 by using thus obtained W3 [g], W4 [g], and W5 [g].

$$FSC\ [g/g] = \{(W4-W5)/W3\} - 1 \qquad [\text{Math. 2}]$$

(5-3) Water Absorption Capacity under Load (AAP)

The water absorption capacity under load (AAP) of the particulate water absorbing agent according to the present invention was measured according to ERT442.2-02.

That is, 0.9 g (W6 [g] in mass) of the particulate water absorbing agent was put in a measuring apparatus, and a mass (W7 [g]) of the entire measuring apparatus (including the particulate water absorbing agent) was measured. Then, the particulate water absorbing agent was caused to absorb a 0.90 wt % sodium chloride aqueous solution under a load of 2.06 kPa (0.3 psi, 21 [g/cm$^2$]) or 4.83 kPa (0.7 psi, 50 [g/cm$^2$]). After 1 hour, a mass (W8 [g]) of the entire measuring apparatus was measured and the water absorption capacity under load (AAP) was calculated by the following Mathematical Formula 3 by using thus obtained W6 [g], W7 [g], and W8 [g].

$$\text{AAP [g/g]} = (W8 - W7)/W6 \qquad \text{[Math. 3]}$$

(5-4) Vertical Diffusion Absorbency Under Load (VDAUP)

The vertical diffusion absorbency under load (VDAUP) of the particulate water absorbing agent according to the present invention was measured as in the above (5-3) except that at this time in (5-4), a used amount of the particulate water absorbing agent was changed to 10.000 g±0.050 g and a condition of the load was changed to 4.83 kPa (0.7 psi, 50 [g/cm$^2$]) from those in the measurement of the water absorption capacity under load (AAP) in the above (5-3).

That is, 10.000 g±0.050 g of the particulate water absorbing agent was put in a measuring apparatus, and a mass (W9 [g]) of the entire measuring apparatus (including the particulate water absorbing agent) was measured. Then, the particulate water absorbing agent was caused to absorb a 0.90 wt % sodium chloride aqueous solution under a load of 4.83 kPa (0.7 psi, 50 [g/cm$^2$]). After 1 hour, a mass (W10 [g]) of the measuring apparatus was measured and the vertical diffusion absorbency under load (VDAUP) was calculated by the following Mathematical Formula 4 by using thus obtained W9 [g] and W10 [g].

$$\text{VDAUP [g]} = W10 - W9 \qquad \text{[Math. 4]}$$

(5-5) Water Soluble Component (Ext)

The water soluble component (Ext) of the particulate water absorbing agent according to the present invention was measured according to ERT470.2-02.

That is, into a plastic container (capacity: 250 mL) with a lid which plastic container is provided therein with a rotor having a length of 35 mm, 1.0 g of the particulate water absorbing agent and 200.0 g of a 0.90 wt % sodium chloride aqueous solution are put in and stirred for 16 hours in an atmosphere at a temperature in a range of 20° C. to 25° C. (room temperature) and at a relative humidity of 50 RH %±5 RH %. Then, a water soluble component in the particulate water absorbing agent was extracted. Next, thus obtained extract was filtered by use of one sheet of paper filter (ADVANTEC Toyo Kaisha, Ltd., Co., Product Name: JIS P 3801, No. 2, Thickness: 0.26 mm, retained particle diameter: 5 μm), and 50.0 g of thus obtained filtrate was used for measurement. Then, this liquid for measurement was titrated with a 0.1 N—NaOH aqueous solution until pH becomes pH10. Thereafter, a resultant liquid was further titrated with a 0.1 N—HCl aqueous solution until pH becomes pH2.7. Then, respective titers ([NaOH] mL, [HCl] mL) were obtained.

The same operation was carried out with respect to only a 0.90 wt % sodium chloride aqueous solution, and thereby a blank titre ([bNaOH] mL, [bHCl] mL) was obtained.

In the case of the particulate water absorbing agent of the present invention, the water soluble component (Ext) was calculated by the following Mathematical Formula 5 based on an average molecular weight of a monomer in use and the titres obtained by the above operation.

$$\text{Ext[MASS \%]} = 0.1 \times (\text{AVERAGE MOLECULAR WEIGHT OF MONOMER}) \times 200.0 \times 100 \times \{[\text{HCl}] - [\text{bHCl}]\}/1000/1.0/50.0 \qquad \text{[Math. 5]}$$

Note that in a case where the average molecular weight of the monomer is unknown, the average molecular weight of the monomer was calculated by use of a neutralization rate obtained by the above titration operation. Note that the neutralization rate was obtained by the following Mathematical Formula 6.

$$\text{NEUTRALIZATION RATE [MOL \%]} = \{1 - ([\text{NaOH}] - [\text{bNaOH}])/([\text{HCl}] - [\text{bHCl}])\} \times 100 \qquad \text{[Math. 6]}$$

(5-6) pH

The pH of the particulate water absorbing agent according to the present invention was measured according to ERT400.2-02.

That is, into a beaker (capacity: 250 mL), 100 mL of a 0.9 wt % sodium chloride aqueous solution was put in and then gently stirred (for example, at a rotational speed of 100 rpm) by use of a magnetic stirrer (length: 30 mm, outer diameter: 6 mm) in an atmosphere at a temperature in a range of 20° C. to 25° C. (room temperature) and a relative humidity of 50 RH %±5 RH %. Into this state, 0.5 g of the particulate water absorbing agent was further put in and the stirring was further continued. After 10 minutes, rotation of the magnetic stirrer was stopped and a resultant dispersion liquid was left still. After one minute, a pH electrode was immersed into a supernatant part of the dispersion liquid and pH was measured. The pH electrode used here was one that was calibrated in standard solutions having pH4.0 and pH7.0, respectively.

(5-7) Moisture Content

The moisture content of the particulate water absorbing agent according to the present invention was measured according to ERT430.2-02.

That is, 1.00 g of the particulate water absorbing agent was weighed and taken in an aluminum cup whose bottom surface has a diameter of approximately 50 mm, and then, a total mass W11 [g] of thus obtained sample (particulate water absorbing agent and aluminum cup) was measured.

Next, the sample was left still in a calm oven in which a temperature of an atmosphere was 105° C., so that the particulate water absorbing agent was dried. After three hours, the sample was taken out from the oven and cooled down to a room temperature in a desiccator. Thereafter, a total mass W12 [g] of thus dried sample (the particulate water absorbing agent and the aluminum cup after drying) was measured. Then, the moisture content [mass %] was calculated by the following Mathematical Formula 7.

$$\text{MOISTURE CONTENT [WEIGHT \%]} = (W11 - W12)/(\text{WEIGHT OP PARTICULATED WATER-ABSORBENT AGENT}) \times 100 \qquad \text{[Math. 7]}$$

Note that in a case where a physical property of the particulate water absorbing agent needs to be subjected to correction of a solid content, the temperature for drying was changed to 180° C. and the moisture content (solid content) was calculated. The moisture content and the solid content have a relation as in the following Mathematical Formula 8.

$$\text{SOLID CONTENT [WEIGHT \%]} = 100 - (\text{MOISTURE CONTENT}) \qquad \text{[Math. 8]}$$

(5-8) Mass Average Particle Diameter (D50), Logarithmic Standard Deviation (σζ) of Particle Size Distribution, and Percentage (Particle Content) by Mass of Particles Having Particle Diameter of Less Than 150 μm The mass average particle diameter (D50), the logarithmic standard deviation (σζ) of the particle size distribution and the percentage (particle content rate) by mass of particles having a particle diameter of less than 150 μm of the particulate water absorbing agent according to the present invention were measured according to a measurement method disclosed in European Patent No. 0349240.

That is, by use of JIS standard sieves (The IIDA TESTING SIEVE: 80 mm in inner diameter; JIS Z8801-1 (2000)) respectively having mesh sizes of 850 µm, 710 µm, 600 µm, 500 µm, 425 µm, 300 µm, 212 µm, 150 µm, 106 µm, and 75 µm or sieves corresponding to such JIS standard sieves, 10.00 g of the particulate water absorbing agent were classified. After this classification, a mass of each sieve was measured, so that the percentage (mass %) by mass of particles having a particle diameter of less than 150 µm was calculated. Note that the "percentage by mass of particles having a particle diameter of less than 150 µm" means a percentage by mass of particles capable of passing through a JIS standard sieve having a mesh size of less than 150 µm, relative to a whole of the particulate water absorbing agent. Further, a graph of a residual percentage R of each particle size mentioned above was plotted on a sheet of logarithmic probability paper, and a particle diameter corresponding to R=50 mass % was read as the mass average particle diameter (D50) from the graph. Note that the mass average particle diameter (D50) means a particle diameter of a standard sieve corresponding to 50 mass % of the whole of the particulate water absorbing agent.

Further, the logarithmic standard deviation ($\sigma\zeta$) of the particle size distribution was calculated by the following Mathematical Formula 9. Note that a smaller value of the logarithmic standard deviation ($\sigma\zeta$) of the particle size distribution indicates a narrower particle size distribution.

$$\sigma\zeta = 0.5 \times \ln(X2/X1) \qquad \text{[Math. 9]}$$

Note that X1 indicates a particle diameter corresponding to R=84.1 mass %, while X2 indicates a particle diameter corresponding to R=15.9 mass %.

(5-9) Multivalent Metal Cation in Particulate Water Absorbing Agent

The multivalent metal cation in the particulate water absorbing agent according to the present invention was measured according to "a method of determining a quantity of a multivalent metal component contained in a water absorbent resin" as disclosed in Japanese Patent Application Publication, Tokukai, No. 2005-113117.

In other words, first, 1.0 g of the particulate water absorbing agent was weighed and taken in a polypropylene beaker whose capacity was 260 mL, and 190.0 g of a physiological saline solution (0.9 wt % sodium chloride aqueous solution) and 10.0 g of 2N hydrochloric acid were added. Then, stirring was carried out for 30 minutes at a room temperature. After the stirring, a supernatant solution was filtered via a chromate disc (GL Chromato Disc 25A, GL Sciences, Inc.). Further, a resultant filtrate was analyzed by use of a plasma emission spectrometer (manufactured by Horiba, Ltd., ULTIMA) so that a concentration of the multivalent metal cation was calculated. Note that a calibration curve was prepared by use of a physiological saline solution containing a known amount of the multivalent metal cation. The concentration of the multivalent metal cation in the particulate water absorbing agent is expressed by the following Mathematical Formula 10, based on the concentration of the multivalent metal cation which concentration had been calculated above.

$$\text{CONCENTRATION OF MULTIVALENT METAL CATION IN PARTICULATED WATER-ABSORBENT AGENT [WEIGHT \%]} = \text{CONCENTRATION OF MULTIVALENT METAL CATION IN SOLUTION} \times 200.0 \qquad \text{[Math. 10]}$$

(5-10) Measurement of Dust Amount

Measurement of a dust amount was carried out according to the description in paragraphs [0281] and [0282] of Pamphlet of PCT International Publication No. WO2006/098271. In other words, the dust amount of the water absorbing agent was measured under the following conditions, on the basis of an increase in mass of the dust suctioned and caught by a glass fiber filter paper within a predetermined period. A measuring apparatus here was Heubach DUSTMETER manufactured by German Heubach Engineering GmbH, and a measurement mode Type II was used for measurement here. The measurement was carried out as follows in an atmosphere at a temperature of 23° C. (±2° C.), at a relative humidity of 20% to 40%, and under a normal pressure.

(1) Put 100.00 g of the water absorbing agent as a measurement sample, into a rotatable drum.

(2) Measure a mass ([Da] g) of a glass fiber paper filter (e.g., manufactured by ADVANTEC, GLASS FIBER, GC-90 or an equivalent processed to have a diameter of 50 mm) whose retained particle diameter is 0.5 µm (JIS P3801) and diameter is 50 mm, to 0.00001 g accuracy.

(3) Fix a large particle centrifuge 201 to the rotatable drum, and further a filter case to which the glass fiber paper filter is mounted.

(4) Set measurement conditions in a control section of the dust meter as follows and carry out measurement: a rotational speed of the drum: 30 R/min, suction air volume: 4 L/min, and Time (measurement time): 30 min.

(5) After a predetermined time has elapsed, measure a mass ([Db]) of the glass fiber paper filter to 0.00001 g accuracy.

The dust amount is calculated as follows, by use of the Da and the Db above.

$$\text{Dust Amount [mg/kg]} = ([Db]-[Da])/100 \times 1000000$$

(5-11) Measurement of Dust Amount after Heat Treatment

The dust amount after heat treatment in the present invention is the dust amount of the particulate water absorbing agent that has undergone storage at 60° C. for 3 weeks in a sealed container.

More specifically, after 200 g of the particulate water absorbing agent was put and sealed in a polypropylene container (Manufactured by Teraoka Corporation, Pack-Ace P-600) whose internal volume was 600 ml, the entire container including the particulate water absorbing agent was put in a thermostat whose temperature was set at 60° C. After three weeks, the container was taken out from the thermostat, and then left for 2 hours in a place where the temperature was controlled to 23° C.±2° C. and the relative humidity was controlled to 20% to 40%. Thereafter, the container was opened so that the particulate water absorbing agent after heat treatment was taken out from the container. Then, the dust amount was measured according to the method of measuring the dust amount as described above.

(5-12) Mechanical Treatment

The mechanical treatment for evaluation of the particulate water absorbing agent according to the present invention was carried out by use of a paint shaker. The mechanical treatment with use of the paint shaker is carried out by: (i) first, put 10 g of glass beads having a diameter of 6 mm and 30 g of the water absorbent resin particle or particulate water absorbing agent into a glass container (mayonnaise bottle manufactured by Yamamura Glass Co., Ltd.; Product Name: A-29) having a dimension of 6 cm and a height of 11 cm; (ii) closing the container with an attached inside lid and an attached outside lid, (iii) then fix the container to the paint shaker (Toyo Seiki Seisaku-sho, Ltd.; Product No. 488), and (iv) shake the container for 20 minutes at 800 cycle/min (CPM). Note that details of this paint shaker is disclosed in Japanese Patent Application Publication, Tokukaihei, No. 9-235378.

(5-13) Method of Determining Quantity of Stabilizing Agent in Particulate Water Absorbing Agent An example of a method of determining a quantity of the stabilizing agent in the particulate water absorbing agent according to the present invention encompasses gas chromatograph mass spectrometry (GC-MS). The stabilizing agent is extracted from the particulate water absorbing agent by the following method, so that the stabilizing agent in the particulate water absorbing agent according to the present invention is analyzed by GC-MS.

In other words, first, 20 g of the particulate water absorbing agent according to the present invention was put in a glass beaker (capacity: 200 ml), and further, 20 ml of a mixed solvent of methanol and water prepared to have a volume ratio (ethanol and water) of 2:1 was added. Next, this glass beaker was immersed in an ultrasonic cleaner and extraction of the stabilizing agent from the particulate water absorbing agent was carried out for 5 minutes. Then, 150 ml of methanol was further added, and extraction of the stabilizing agent from the particulate water absorbing agent by use of the ultrasonic cleaner was carried out for 10 minutes.

Thereafter, the mixed solvent of methanol and water from which mixed solvent the stabilizing agent had been extracted was separated from the particulate water absorbing agent by filtering. Thereby, a solution in which the stabilizing agent was extracted was obtained. From thus obtained solution, solvents (methanol and water) were removed by use of a rotary evaporator (manufactured by Tokyo Rikakikai Co., Ltd., Type: N-1100S), so that a dry solid material containing the stabilizing agent extracted from the particulate water absorbing agent was obtained. Thus obtained dry solid material was dissolved in 5 ml of methanol and supplied as a sample for GC-MS analysis.

The followings were analysis conditions for GC-MS.
Analyzing device: JMS-K9 manufactured by JEOI Ltd.
Analysis column: HP-5MS 30 m x 0.25 mm 0.25 μm
Column temperature: 40° C. 3 min. Hold
10° C./min.
250° C. 8 min. Hold
Injection temperature: 250° C.
Injection mode: splitless 40:1.2

Further, the following method was used for preparation of a calibration curve used in determination of a quantity of 2,6-di-t-butyl-4-methylphenol.

In other words, first, to 100 parts by mass of the water absorbent resin powder (1) in Example 1 described later, 0.4 part by mass of a 10 mass % polyethylene glycol 400 aqueous solution was added as a hydrophilic polymer compound and mixed. This solution contained 4.0 parts by mass of polyethylene glycol 400 and 36 parts by mass of deionized water. At this time, an amount of 2,6-di-t-butyl-4-methylphenol added as the stabilizing agent was varied as follows: 0 part by mass, 0.0002 part by mass, 0.002 part by mass, and 0.02 part by mass. Thereby, four kinds of water absorbent resin powder each containing a different amount of the stabilizing agent were prepared.

Next, into each of the four kinds of water absorbent resin powder, a mixture liquid of 0.9 part by mass of a 27.5 mass % (8 mass % in terms of aluminum oxide) aluminum sulfate aqueous solution, 0.13 part by mass of a 60 mass % sodium lactate aqueous solution and 0.025 part by mass of propylene glycol was added and mixed. Then, thus obtained resultant mixtures each were dried at 60° C. for 1 hour in a calm condition. In other words, in a calm oven in which the temperature of an atmosphere was 60° C., the four kinds of water absorbent resin powder, to which the above mixture liquid had been added and mixed, were left still and dried for 1 hour. From thus obtained dried material, coarse particles were removed by use of a JIS standard sieve having a mesh size of 850 μm, and thereby, particulate water absorbing agents (A) to (D) for preparation of a calibration curve were obtained.

From thus obtained particulate water absorbing agents (A) to (D) for preparation of the calibration curve, the stabilizing agent was extracted by the above method of extracting the stabilizing agent and a GC-MS analysis was carried out. Then, the calibration curve for determination of a quantity was prepared from an added amount of the stabilizing agent and a peak area of the stabilizing agent which peak area was obtained by GC-MS.

Further, another calibration curve for determining a quantity of 2,6-di-t-butylphenol was prepared as in the above preparation of the calibration curve except that the above described 2,6-di-t-butyl-4-methylphenol was changed to 2,6-di-t-butylphenol.

Production Example 1

In a reactor produced by attaching a lid to a double-arm stainless-steel kneader that had an internal volume of 10 L and that was equipped with two sigma type blades and a jacket, a reaction liquid was obtained by introducing 425.2 g of acrylic acid, 4499.5 g of a 37 mass % sodium acrylate aqueous solution, 538.5 g of pure water, 6.17 g of polyethylene glycol diacrylate (molecular mass: 523) and 0.21 g of trisodium diethylenetriamine pentaacetic acid and then carrying out deaeration for 20 minutes in a nitrogen gas atmosphere.

Next, 28.3 g of a 10 mass % sodium persulfate aqueous solution and 23.6 g of a 0.1 mass % L-ascorbic acid aqueous solution were separately added to the reaction solution while the reaction solution was being stirred. Then, after approximately 25 seconds, polymerization was initiated. While thus obtained water-containing gel-like crosslinked polymer was being crushed, the polymerization was carried out at a temperature in a range of 25° C. to 95° C. After 30 minutes from initiation of the polymerization, the water-containing gel-like crosslinked polymer was taken out from the reactor. Note that grains of thus obtained water-containing gel-like crosslinked polymer were refined to have a diameter of approximately 5 mm or less.

Thus grain-refined water-containing gel-like crosslinked polymer was spread on a metal mesh whose mesh size was 300 μm (50 mesh), dried by use of hot air at 170° C. for 65 minutes (this 170° C. was a temperature of hot air), and then pulverized by using a roll mill. Further, thus obtained water absorbent resin particles were classified by use of a JIS standard sieve having a mesh size of 850 μm and blended. This series of operations gave a water absorbent resin particle (1) whose mass average particle diameter (D50) was 458 μm, whose logarithmic standard deviation (σζ) of the particle size distribution was 0.40, and whose form was an irregularly crushed piece form. Thus obtained water absorbent resin particle (1) had a water absorption capacity without load (CRC) of 42 [g/g], and a water soluble component (Ext) of 13 mass %.

Production Example 2

A water absorbent resin particle (2) was obtained as in Production Example 1, except that a used amount of polyethylene glycol diacrylate (molecular mass: 523) was changed from that in Production Example 1 to 4.93 g. As a result, a water absorbent resin particle (2) obtained here had a mass average particle diameter (D50) of 380 μm, a logarithmic standard deviation (σζ) of the particle size distribution of 0.33 and an irregularly crushed piece form. Thus obtained water absorbent resin particle (2) had a water absorption capacity without load (CRC) of 45 [g/g], and a water soluble component (Ext) of 15 mass %.

Example 1

As a treatment of surface crosslinking, to 100 parts by mass of the water absorbent resin particle (1) obtained in Production Example 1, an aqueous solution of a surface crosslinking agent was uniformly mixed. The aqueous solution of the surface crosslinking agent here contained 0.5 part by mass of propylene glycol, 0.3 part by mass of 1,4-butanediol and 3.0 parts by mass of pure water. Then, heat treatment at 210° C. for 40 minutes was carried out, so that a surface crosslinked water absorbent resin (hereinafter, referred to as "water absorbent resin powder") (1) was obtained. The heat treatment was carried out by stirring the above mixture in a stainless-steel container immersed in an oil bath. Note that the above "210° C." is a temperature of oil in the oil bath.

Next, to 100 parts by mass of the water absorbent resin powder (1), 0.4 part by mass of a 10 mass % polyethylene glycol 600 aqueous solution was added and mixed. This 10 mass % polyethylene glycol 600 aqueous solution contained 4.0 parts by mass of polyethylene glycol 600 as a hydrophilic polymer compound, 0.002 part by mass of 2,6-di-t-butyl-4-methylphenol as a stabilizing agent, and 36 parts by mass of deionized water.

Then, after a mixture liquid of 0.9 part by mass of a 27.5 mass % (8 mass % in terms of aluminum oxide) aluminum sulfate aqueous solution, 0.13 part by mass of a 60 mass % sodium lactate aqueous solution, and 0.025 part by mass of propylene glycol was added and mixed, a resultant mixture was dried at 60° C. for 1 hour in a calm condition. In other words, the water absorbent resin powder (1), to which the above mixture liquid had been added and mixed, was left still and dried for 1 hour in a calm oven in which the temperature of an atmosphere was 60° C. From thus obtained dried material, coarse particles were removed by use of a JIS standard sieve having a mesh size of 850 μm, so that the particulate water absorbing agent (1) was obtained. Table 1 shows composition of this particulate water absorbing agent (1), and Table 2 shows various performances of the particulate water absorbing agent (1).

Example 2

A particulate water absorbing agent (2) was obtained as in Example 1, except that 4.0 parts by mass of polyethylene glycol 600 as the hydrophilic polymer compound was changed to 5.0 parts by mass of polyethylene glycol 400, an amount of deionized water was changed to 35 parts by mass, an amount of 2,6-di-t-butyl-4-methylphenol was changed to 0.0005 part by mass, and an amount of the 10 mass % polyethylene glycol 400 aqueous solution was changed to 0.5 part by mass. Table 2 shows various performances of thus obtained particulate water absorbing agent (2).

Example 3

As a treatment of surface crosslinking, to 100 parts by mass of the water absorbent resin particle (2) obtained in Production Example 2, an aqueous solution of a surface crosslinking agent was uniformly mixed. The aqueous solution of the surface crosslinking agent here contained 0.5 part by mass of propylene glycol, 0.3 part by mass of 1,4-butanediol and 1.0 part by mass of pure water. Then, heat treatment at 210° C. for 40 minutes was carried out, so that a surface crosslinked water absorbent resin (hereinafter, referred to as "water absorbent resin powder") (2) was obtained. The heat treatment was carried out by stirring the above mixture in a stainless-steel container immersed in an oil bath.

Then, to the above 100 parts by mass of the water absorbent resin powder (2), 1.0 part by mass of a 50 mass % polyethylene glycol 4000 aqueous solution was added and mixed. Then, a resultant mixture was dried at 60° C. for 1 hour in a calm condition. The 50 mass % polyethylene glycol 4000 aqueous solution here was prepared by mixing 5.0 parts by mass of polyethylene glycol 4000 as a hydrophilic polymer compound, 0.0005 part by mass of 2,6-di-t-butylphenol as a stabilizing agent, and 5.0 parts by mass of deionized water. In other words, the water absorbent resin powder (2), to which the above aqueous solution had been added and mixed, was left still and dried for 1 hour in a calm oven in which the temperature of an atmosphere was 60° C. Then, a particulate water absorbing agent (3) was obtained by removing, from thus obtained dried material, coarse particles with use of a JIS standard sieve having a mesh size of 850 μm. Table 2 shows various performances of the particulate water absorbing agent (3).

Example 4

A particulate water absorbing agent (4) was obtained as in Example 1, except that 4.0 parts by mass of polyethylene glycol 600 as the hydrophilic polymer compound was changed to 1.0 part by mass of polyethylene glycol 10000, an amount of deionized water was changed to 1.0 part by mass, an amount of 2,6-di-t-butyl-4-methylphenol was changed to 0.00001 part by mass, and an amount of a 50 mass % polyethylene glycol 10000 aqueous solution was 2.0 parts by mass. Table 2 shows various performances of thus obtained particulate water absorbing agent (4).

Example 5

A particulate water absorbing agent (5) was obtained as in Example 3, except that 5.0 parts by mass of polyethylene glycol 4000 as the hydrophilic polymer compound was changed to 1.0 part by mass of polypropylene glycol 1000, an amount of deionized water was changed to 9.0 parts by mass, and an amount of 2,6-di-t-butyl-4-methylphenol was changed to 0.0002 part by mass. Table 2 shows various performances of thus obtained particulate water absorbing agent (5).

Example 6

A particulate water absorbing agent (6) was obtained as in Example 1, except that that 4.0 parts by mass of polyethylene glycol 600 as the hydrophilic polymer compound was changed to 5.0 parts by mass of methoxypolyethylene glycol 400, an amount of deionized water was changed to 35 parts by mass, an amount of 2,6-di-t-butyl-4-methylphenol was changed to 0.005 part by mass, and an amount of a 10 mass % polyethylene glycol 400 aqueous solution was 0.5 part by mass. Table 2 shows various performances of thus obtained particulate water absorbing agent (6).

Example 7

A particulate water absorbing agent (7) was obtained as in Example 1, except that 0.3 part by mass of 1,4-butanediol in the treatment of surface crosslinking was changed to 0.3 part by mass of ethylene carbonate. Table 2 shows various performances of thus obtained particulate water absorbing agent (7).

Example 8

A particulate water absorbing agent (8) was obtained as in Example 1, except that the aqueous solution of the surface crosslinking agent which aqueous solution contained 0.5 part by mass of propylene glycol, 0.3 part by mass of 1,4-butanediol and 3.0 parts by mass of pure water in the treatment of surface crosslinking was changed to an aqueous solution of a surface crosslinking agent which aqueous solution contained 0.5 part by mass of propylene glycol, 0.3 part by mass of ethylene carbonate, 0.02 part by mass of ethyleneglycol diglycidyl ether (DENACOL EX-810) and 3.0 parts by mass of pure water. Table 2 shows various performances of thus obtained particulate water absorbing agent (8).

Example 9

A particulate water absorbing agent (9) was obtained by filling 300 g of the particulate water absorbing agent (1) obtained in Example 1 in a polypropylene sealed container having an internal volume of 500 ml and storing this container indoors for three months under conditions where a temperature was controlled to 25° C. and a relative humidity was controlled to 50%. Table 3 shows various performances of thus obtained particulate water absorbing agent (9).

Example 10

A particulate water absorbing agent (10) was obtained as in Example 9, except that the particulate water absorbing agent (1) was changed to the particulate water absorbing agent (2) obtained in Example 2. Table 3 shows various performances of thus obtained particulate water absorbing agent (10).

Comparative Example 1

A comparative particulate water absorbing agent (1) was obtained as in Example 1, except that the hydrophilic polymer compound was not used. Table 2 shows various performances of thus obtained comparative particulate water absorbing agent (1).

Comparative Examples 2 to 7

Comparative particulate water absorbing agents (2) to (7) were obtained as in Examples 1 to 6, respectively, except that the stabilizing agent was not used. Table 2 shows various performances of each of thus obtained comparative particulate water absorbing agents (2) to (7).

Comparative Example 8

A comparative particulate water absorbing agent (8) was obtained, by a method as in Example 1 described in Patent Literature 1 (Japanese Patent Application Publication, Tokukai, No. 2008-125716). More specifically, 330 parts of polyhexamethylene carbonate diol having a number average molecular weight (Mn1) of 2000, 6.5 parts of 2,2-dimethylol propionic acid (DMPA), 98 parts of 4,4'-dicyclohexylmethane diisocyanate and 235 parts of acetone were reacted at 90° C. for 10 hours in a nitrogen gas atmosphere, while being uniformly mixed. Thereby, an acetone solution of an NCO-terminated urethane prepolymer was obtained, which is followed by cooling of this acetone solution to 40° C. Then, 5.0 parts of triethylamine was added and emulsified by stirring with use of a homomixer for 1 minute. Thereafter, an aqueous solution containing 1.0 part of ethylenediamine and 230 parts of water was added, so that a chain extension reaction was carried out.

Then, acetone was distilled away under reduced pressure and a concentration was controlled with water, so that an urethane resin (C-1) emulsion was obtained. This emulsion had a concentration of 40%, and a volume average particle diameter of 0.5 μm. Then, after 0.25 part of thus obtained urethane resin (C-1) emulsion (emulsion concentration: 40%) was diluted with 5 parts of methanol and water (volume ratio of methanol:water=4:6) so that a diluted emulsion was obtained. Then, a full amount of thus obtained diluted emulsion was sprinkled over 100 parts by mass of the water absorbent resin powder (1) obtained in the process of Example 1 of the present specification and uniformly mixed. From thus obtained mixture, coarse particles were removed by use of a JIS standard sieve having a mesh size of 850 μm. As a result, the comparative particulate water absorbing agent (8) was obtained.

Comparative Example 9

A comparative particulate water absorbing agent (9) was obtained, by a method as in Example 1 described in Patent Literature 2 (Japanese Translation of PCT International Application, Tokuhyou, No. 2006-528544). More specifically, to 100 parts by mass of the water absorbent resin particle (1) obtained in Production Example 1, 1.0 part by mass of magnesium hydrogen phosphate trihydrate, and 0.5 part by mass of thermoplastic polyester (manufactured by Schaetti AG, Product Code: Schaetti Fix 386) as a thermoplastic adhesive were mixed. Further, 4 parts by mass of a 25 mass % ethylene carbonate aqueous solution was uniformly mixed and heat treatment at 195° C. for 90 minutes was carried out. By removing coarse particles from thus obtained heat-treated material with use of a JIS standard sieve having a mesh size of 850 μm, the comparative particulate water absorbing agent (9) was obtained.

Comparative Example 10

A comparative particulate water absorbing agent (10) was obtained, by a method as in Example 1 described in Patent Literature 3 (Pamphlet of PCT International Publication No. WO95/33558). More specifically, to 100 parts by mass of the water absorbent resin particle (1) obtained in Production Example 1, an aqueous solution of a surface crosslinking agent was uniformly mixed. The aqueous solution of the surface crosslinking agent contained 0.5 part by mass of propylene glycol, 0.3 part by mass of 1,4-butanediol, and 3.0 parts by mass of pure water. Then, heat treatment was carried out at 210° C. for 40 minutes. As a result, a surface crosslinked water absorbent resin (hereinafter, referred to as "water absorbent resin powder") (1) was obtained.

Then, into 100 parts by mass of the water absorbent resin powder (1), 0.2 part by mass of amino-modified silicone oil [manufactured by Shin-Etsu Chemical Co., Ltd., "KF-880" (surface tension: 21.3 dynes/cm; viscosity: 650 cps; average molecular weight: approximately 20,000)] was added and mixed. From thus obtained mixture, coarse particles were removed with use of a JIS standard sieve having a mesh size of 850 μm. Thereby, the comparative particulate water absorbing agent (10) was obtained. Table 2 shows various performances of the comparative particulate water absorbing agent (10).

Comparative Example 11

A comparative particulate water absorbing agent (11) was obtained as in Example 1, except that: the 10 mass % polyethylene glycol 600 aqueous solution containing 4.0 parts by mass of polyethylene glycol 600 and the stabilizing agent was changed to 2.0 parts by mass of a 3.3 mass % aqueous solution of VORANO 1230-238 (registered trademark, manufactured by Dow Chemical Company: polypropoxylated glycerin) used in Patent Literature 12; and the mixture liquid containing aluminum sulfate was changed to 2 parts by mass of powder aluminum sulfate tetradecahydrate. Table 2 shows various performances of the comparative particulate water absorbing agent (11).

Comparative Example 12

A comparative particulate water absorbing agent (12) was obtained as in Example 9, except that the particulate water absorbing agent (1) was changed to the comparative particulate water absorbing agent (2) obtained in Comparative Example 2. Table 3 shows various performances of the comparative particulate water absorbing agent (12).

Comparative Example 13

A comparative particulate water absorbing agent (13) was obtained as in Example 9, except that the particulate water absorbing agent (1) was changed to the comparative particulate water absorbing agent (3) obtained in Comparative Example 3. Table 3 shows various performances of the comparative particulate water absorbing agent (13).

TABLE 1

| | | Water Absorbent Resin Particle | Hydrophilic Polymer | | | | Multivalent Cation | Stabilizing Agent | | |
|---|---|---|---|---|---|---|---|---|---|---|
| | | | Kind | Amount (part by mass) | Concentration (mass %) | Additive Amount (1) (part(s) by mass) | Additive Amount (1) (part(s) by mass) | Kind | Additive Amount (2) (ppm by mass) | Additive Amount (3) (ppm by mass) |
| Example | 1 | (1) | PEG600 | 0.04 | 10 | 0.4 | 1 | 1 | 500 | 0.2 |
| | 2 | (1) | PEG400 | 0.05 | 10 | 0.5 | 1 | 1 | 100 | 0.05 |
| | 3 | (2) | PEG4000 | 0.5 | 50 | 1 | 0 | 2 | 100 | 0.5 |
| | 4 | (1) | PEG10000 | 1 | 50 | 2 | 1 | 1 | 50 | 0.5 |
| | 5 | (2) | Poly-PG1000 | 0.05 | 10 | 0.5 | 0 | 2 | 200 | 0.1 |
| | 6 | (2) | M-PEG350 | 0.05 | 10 | 0.5 | 0 | 1 | 1000 | 0.5 |
| | 7 | (1) | PEG600 | 0.04 | 10 | 0.4 | 1 | 1 | 500 | 0.2 |
| | 8 | (2) | PEG600 | 0.04 | 10 | 0.4 | 1 | 1 | 500 | 0.2 |
| Comparative Example | 1 | (1) | None | 0 | 0 | 0 | 1 | 1 | — | 0.2 |
| | 2 | (1) | PEG600 | 0.04 | 10 | 0.4 | 1 | — | 0 | 0 |
| | 3 | (1) | PEG400 | 0.05 | 10 | 0.5 | 1 | — | 0 | 0 |
| | 4 | (2) | PEG4000 | 0.5 | 50 | 1 | 0 | — | 0 | 0 |
| | 5 | (1) | PEG10000 | 1 | 50 | 2 | 1 | — | 0 | 0 |
| | 6 | (2) | Poly-PG1000 | 0.05 | 10 | 0.5 | 0 | — | 0 | 0 |
| | 7 | (2) | M-PEG350 | 0.05 | 10 | 0.5 | 0 | — | 0 | 0 |
| | 8 | (1) | Urethane Resin | 0.25 | | | 0 | — | 0 | 0 |
| | 9 | (1) | Thermoplastic Polyester | 0.5 | | | 0 | — | 0 | 0 |
| | 10 | (1) | amino-modified silicone | 0.2 | | | 0 | — | 0 | 0 |
| | 11 | (1) | VORANOL 230-238 | 0.066 | 3.3 | 2 | 2* | — | 0 | 0 |

In Table 1, "(1)" in a column of "Water Absorbent Resin Particle" indicates the water absorbent resin particle (1) produced in Production Example 1, while "(2)" indicates the water absorbent resin particle (2) obtained in Production Example 2.

In a column of hydrophilic polymer, "Kind" indicates a kind of hydrophilic polymer employed. In the column, "PEG" indicates polyethylene glycol, "Poly-PG" indicates polypropylene glycol, and "M-PEG" indicates "methoxy-polyethylene glycol".

In the column of hydrophilic polymer, "Amount (part by mass)" indicates part by mass of the hydrophilic polymer contained in a hydrophilic polymer aqueous solution employed, relative to 100 parts by mass of the water absorbent resin powder employed. For example, in Example 1, 0.4 part by mass of the 10 mass % polyethylene glycol 600 aqueous solution is added and mixed, with respect to 100 parts by mass of the water absorbent resin powder (1). Accordingly, a ratio of polyethylene glycol 600 in the aqueous solution is 0.04 part by mass with respect to 100 parts by mass of the water absorbent resin powder (1). Therefore, "0.04" is written as the "Amount (part by mass)".

In the column of hydrophilic polymer, "Concentration (mass %)" means mass % of the hydrophilic polymer contained in the hydrophilic polymer aqueous solution employed. For example in Example 1, the 10 mass % polyethylene glycol 600 aqueous solution is employed. Accordingly, "10" is written as "Concentration (mass %)".

In the column of the hydrophilic polymer, "Additive Amount (1) (part(s) by mass)" is part(s) by mass of the hydrophilic polymer aqueous solution employed, relative to 100 parts by mass of the water absorbent resin powder employed. For example, in Example 1, 0.4 part by mass of the 10 mass % polyethylene glycol 600 aqueous solution is added and mixed with respect to 100 parts by mass of the water absorbent resin powder (1). Accordingly, "0.4" is written as "Additive Amount (1) (part(s) by mass)".

In Table 1, "Additive Amount (1) (part(s) by mass)" in a column of "Multivalent Cation" indicates part(s) by mass of a mixture liquid containing a multivalent metal cation relative to 100 parts by mass of the water absorbent resin powder (1) employed. For example, in Example 1, the mixture liquid containing 0.9 part by mass of the 27.5 mass % (8 mass % in terms of aluminum oxide) aluminum sulfate aqueous solution, 0.13 part by mass of the 60 mass % sodium lactate aqueous solution and 0.025 part by mass of propylene glycol is added and mixed with respect to 100 parts by mass of the water absorbent resin powder (1). Because the above 0.9 part by mass+the above 0.13 part by mass+the above 0.025 part by mass=1.055 parts by mass, "1" is written as the above "additive amount (1) (parts by mass)".

In Table 1, as to "Kind" in a column of the stabilizing agent, "1" indicates 2,6-di-t-butyl-4-methylphenol, while "2" indicates 2,6-di-t-butylphenol.

In the column of the stabilizing agent, "Additive Amount (2) (ppm by mass)" indicates ppm by mass of the stabilizing agent contained in the hydrophilic polymer aqueous solution with respect to parts by mass of the hydrophilic polymer in the hydrophilic polymer aqueous solution. For example, in Example 1, the 10 mass % polyethylene glycol 600 aqueous solution is employed as the hydrophilic polymer aqueous solution. An amount of polyethylene glycol 600 contained in the aqueous solution is 4.0 parts by mass, while the stabilizing agent contained in the aqueous solution is 0.002 part by mass. Accordingly, 0.002/4=500 ppm by mass. Therefore, "500" is written as the "additive amount (2) (ppm by mass)".

In a column of the stabilizing agent, "Additive Amount (3) (ppm by mass)" is ppm by mass of the stabilizing agent contained in the hydrophilic polymer aqueous solution employed, relative to 100 parts by mass of the water absorbent resin powder employed. For example, in Example 1, 0.4 part by mass of the 10 mass % polyethylene glycol 600 aqueous solution is added and mixed with respect to 100 parts by mass of the water absorbent resin powder (1). A ratio of the stabilizing agent contained in this aqueous solution is $0.002/(4.0+0.002+36)$=approximately $5.0 \times 10^{-5}$. Accordingly, as a result of calculation of a product of this value and the above 0.4 part by mass, a ratio of the stabilizing agent in the aqueous solution is found to be approximately 0.2 ppm by mass, relative to 100 parts by mass of the water absorbent resin powder (1). Therefore, "0.2" is written as the "Additive Amount (3) (ppm by mass)".

Further, in Comparative Example 1, with respect to 100 parts by mass of the water absorbent resin powder (1), 0.4 part by mass of an aqueous solution that contains 0.002 part by mass of the stabilizing agent and 36 parts by mass of deionized water but that contains no polyethylene glycol 600 is added and mixed. However, no hydrophilic polymer is contained in the aqueous solution. Therefore, in the column of the hydrophilic polymer in Table 1, "0" is written in the column of "Additive Amount (1)". A ratio of the stabilizing agent contained in the aqueous solution is $0.002/(0.002+36)$ =approximately $5.555 \times 10^{-5}$. Therefore, as a result of calculation of a product of this value and the above 0.4 part by mass, a ratio of the stabilizing agent in the aqueous solution relative to 100 parts by mass of the water absorbent resin powder (1) is found to be approximately 0.2 ppm by mass. Therefore, "0.2" is written as "Additive Amount (3) (ppm by mass)".

Note that compounds used in Comparative Examples 8 to 10 in the column of the hydrophilic polymer are non-hydrophilic polymers. Further, "Additive Amount (1)" of the multivalent cation of Comparative Example 11 indicates an added amount of the powder aluminum sulfate tetradecahydrate and written as "2*" in Table 1.

TABLE 2

|  |  | After Mechanical Treatment (mg/kg) | After Heat Treatment (mg/kg) | CRC (g/g) | FSC (g/g) | AAPO.3 (g/g) | AAPO.7 (g/g) | VDAUP (g) | Mass Average Particle Diameter (D50) (μm) | Stabilizing Agent Quantitative Determination Result (with respect to Particulate Water Absorbing Agent) (ppm by mass) |
|---|---|---|---|---|---|---|---|---|---|---|
| Example | 1 | 5 | 15 | 33 | 56 | 32 | 25 | 62 | 465 | 0.18 |
|  | 2 | 5 | 14 | 33 | 57 | 32 | 25 | 56 | 450 | 0.042 |
|  | 3 | 15 | 28 | 35 | 51 | 35 | 20 | 44 | 395 | 0.35 |
|  | 4 | 20 | 29 | 33 | 54 | 32 | 25 | 56 | 470 | 0.44 |
|  | 5 | 10 | 20 | 35 | 51 | 35 | 20 | 41 | 375 | 0.10 |
|  | 6 | 10 | 14 | 35 | 52 | 35 | 21 | 44 | 401 | 0.41 |
|  | 7 | 5 | 14 | 33 | 56 | 32 | 25 | 62 | 473 | 0.16 |
|  | 8 | 6 | 14 | 33 | 57 | 32 | 25 | 62 | 386 | 0.17 |
| Comparative Example | 1 | 80 | 120 | 33 | 47 | 32 | 25 | 56 | 503 | 0.16 |
|  | 2 | 5 | 32 | 33 | 56 | 32 | 25 | 62 | 490 | 0 |
|  | 3 | 5 | 30 | 33 | 57 | 32 | 25 | 56 | 485 | — |
|  | 4 | 15 | 70 | 35 | 51 | 35 | 20 | 44 | 377 | — |
|  | 5 | 20 | 93 | 33 | 54 | 32 | 25 | 56 | 455 | — |
|  | 6 | 10 | 83 | 35 | 51 | 35 | 20 | 41 | 390 | — |
|  | 7 | 10 | 35 | 35 | 52 | 35 | 21 | 44 | 392 | — |
|  | 8 | 30 | 70 | 32 | 46 | 29 | 21 | 32 | 510 | — |
|  | 9 | 55 | 80 | 32 | 47 | 27 | 18 | 29 | 475 | — |
|  | 10 | 25 | 65 | 32 | 47 | 27 | 17 | 29 | 466 | — |
|  | 11 | 35 | 50 | 31 | 50 | 31 | 22 | 50 | 460 | — |

Table 2 shows various performances of the particulate water absorbing agents (1) to (8) obtained in Examples 1 to 8 and the comparative particulate water absorbing agents (1) to (11) obtained in Comparative Examples 1 to 11.

In Table 2, "After Mechanical Treatment" indicates a dust amount that is calculated according to the above section (5-10) after the mechanical treatment as described in the section (5-12). The wording "After Heat Treatment" indicates a dust amount calculated according to the section (5-10) after the heat treatment as described in the section (5-11). The "CRC" indicates the water absorption capacity without load. The "FSC" indicates the water absorption capacity without load after hanging. The "AAP0.3" indicates a water absorption capacity under load in a case where the 0.90 wt % sodium chloride aqueous solution is absorbed under a load of 0.3 psi. Further, the "AAP0.7" indicates a water absorption capacity under load in a case where the sodium chloride aqueous solution is absorbed under a load of 0.7 psi. The "VDAUP" indicates a vertical diffusion absorbency under load.

In each Example, the surface tension was approximately 72 mN/m.

In Table 2, "Stabilizing Agent Quantitative Determination Result (with respect to Particulate Water Absorbing Agent) (ppm by mass)" indicates a result of determining a quantity of the stabilizing agent (unit: ppm by mass) in the particulate water absorbing agent, based on the calibration curve obtained as in the above section (5-13).

In a case where no polymer compound is added as in the case of Comparative Example 1 (dust reduction by surface crosslinking equivalent to that described in Patent Literature 15) or in a case where non-hydrophilic polymer (compounds equivalent to those described in Patent Literatures 1 to 3) is added (Comparative Example 8 to 11), the dust amount as a result of the mechanical treatment becomes very large, and the dust amount after the heat treatment also becomes very large. It is clear from Comparative Examples 2 to 7, that in a case where a hydrophilic polymer (compounds equivalent to those described in Patent Literatures 8, 9, 12, and 13) is added but no stabilizing agent is added, the dust amount after the heat treatment becomes large.

(5-12) is carried out. The results shown in the columns of "After Mechanical Treatment" and "After Heat Treatment" are transcriptions of measurement results of respective dust amounts of the particulate water absorbing agents (1) and (2) and the comparative particulate water absorbing agents (2) and (3) as shown in Table 2.

Table 3 shows, in a column of "After Three Months", measurement results of respective dust amounts of the particulate water absorbing agents (9) and (10) and the comparative particulate water absorbing agents (12) and (13) prior to and after the mechanical treatment and after the heat treatment.

In comparison between Example 9 and Comparative Example 12 and between Example 10 and Comparative Example 13, no difference was observed in power dust amount due to mechanical treatment immediately after production. However, after a three-month storage, the dust amount of each of these Comparative Examples is approximately twice as much as the dust amount of Example to be compared. This trend is in good conformity with the trend after heat treatment immediately after production. This result clearly indicates that the particulate water absorbing agent according to the present invention exhibits significant reduction in dust amount as an effect and also that by carrying out a "method for evaluating an increase over time in dust amount of the particulate water absorbing agent according to the present invention", the above effect can be verified in three weeks after production. That is, it is clear that the difference after three months can be evaluated in three weeks.

In other words, it is clear that the effects of the invention of the present application can be obtained for the first time by causing the hydrophilic polymer compound and the stabilizing agent to be present in a localized manner in the vicinity of a surface of a particulate water absorbing agent.

INDUSTRIAL APPLICABILITY

The particulate water absorbing agent according to the present invention is suitably applied to hygiene materials such as disposable diapers, sanitary napkins, and incontinence pads.

TABLE 3

| | Immediately After Production | | | After Three Months | | |
|---|---|---|---|---|---|---|
| | Prior To Mechanical Treatment mg/kg | After Mechanical Treatment mg/kg | After Heat Treatment mg/kg | Prior To Mechanical Treatment mg/kg | After Mechanical Treatment mg/kg | After Heat Treatment mg/kg |
| Example 9 | 1 | 5 | 15 | 2 | 6 | 17 |
| Example 10 | 1 | 5 | 14 | 2 | 6 | 17 |
| Comparative Example 12 | 1 | 5 | 32 | 2 | 12 | 41 |
| Comparative Example 13 | 1 | 5 | 30 | 2 | 12 | 38 |

Table 3 shows, in a column of "Immediately After Production", results of measurement of respective dust amounts of the particulate water absorbing agents (1) and (2) and the comparative particulate water absorbing agent (2) and (3) that are respective materials for the particulate water absorbing agents (9) and (10) and the comparative particulate water absorbing agents (12) and (13) respectively produced in Examples 9 and 10 and Comparative Examples 12 and 13.

In Table 3, "Prior To Mechanical Treatment" shows results of measuring dust amounts in a case where no mechanical treatment as described in the above section

The invention claimed is:
1. A particulate water absorbing agent comprising:
a polyacrylic acid (salt)-based water absorbent resin as a main component;
a hydrophilic polymer compound; and
a stabilizing agent,
the polyacrylic acid (salt)-based water absorbent resin being surface-crosslinked,
the hydrophilic polymer compound being a polymer compound 1 g or more of which is dissolvable in 100 g of water at 25° C., the stabilizing agent being a thioether-based stabilizing agent, a phosphoric acid-based stabilizing agent, a phenol-based stabilizing agent, a combination of a phenol-based stabilizing agent and a thioether-based stabilizing agent, or a combination of a phenol-based stabilizing agent and a phosphoric acid-based stabilizing agent, the phosphoric acid-based stabilizing agent being a stabilizing agent selected from tris(2,4-di-t-butylphenyl) phosphite, 2-[[2,4,8,10-tetrakis(1,1-dimethylethyl)dibenzo[d,f][1,3,2]dioxaphosphepin-6-yl]oxy]-N,N-bis[2-[[2,4,8,10-tetrakis(1,1dimethylethyl)dibenzo[d,f][1,3,2]dioxaphosphepin-6-yl]oxy]-ethyl]ethanamine, diphenyl tridecyl phosphite, triphenyl phosphite, 2,2-methylenebis(4,6-di-t-butylphenyl)octylphosphite, bis(2,6-di-t-butyl-4-methylphenyl)pentaerythritol diphosphite, distearylpentaerythritol diphosphite, and cyclic neopentanetetraylbis(2,6-di-t-butyl-4-methylphenyl) phosphite, and wherein a dust amount after mechanical treatment is less than 30 mg/kg, and a dust amount after heat treatment at 60° C. for 3 weeks is less than 30 mg/kg.

2. The particulate water absorbing agent as set forth in claim 1, wherein a content of the hydrophilic polymer compound is 0.01 part by mass to 5.0 parts by mass relative to 100 parts by mass of the polyacrylic acid (salt)-based water absorbent resin.

3. The particulate water absorbing agent as set forth in claim 1, wherein a content of the stabilizing agent is 0.01 ppm by mass to 10 ppm by mass relative to the polyacrylic acid (salt)-based water absorbent resin.

4. The particulate water absorbing agent as set forth in claim 1, further comprising a water-soluble non-polymer compound.

5. The particulate water absorbing agent as set forth in claim 1, further comprising a multivalent metal cation.

6. The particulate water absorbing agent as set forth in claim 1, further comprising a surfactant.

7. The particulate water absorbing agent as set forth in claim 1, wherein a moisture content is 1 mass % to 15 mass %.

8. The particulate water absorbing agent as set forth in claim 1, wherein a vertical diffusion absorbency under load is 30 g or higher.

* * * * *